(12) United States Patent
Kuechler et al.

(10) Patent No.: US 9,242,918 B2
(45) Date of Patent: *Jan. 26, 2016

(54) DEHYDROGENATION PROCESSES AND PHENOL COMPOSITIONS

(75) Inventors: Keith H. Kuechler, Friendswood, TX (US); Francisco M. Benitez, Cypress, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 243 days.

This patent is subject to a terminal disclaimer.

(21) Appl. No.: 13/814,873

(22) PCT Filed: Aug. 16, 2011

(86) PCT No.: PCT/US2011/047829
§ 371 (c)(1),
(2), (4) Date: May 2, 2013

(87) PCT Pub. No.: WO2012/036819
PCT Pub. Date: Mar. 22, 2012

(65) Prior Publication Data
US 2013/0296614 A1    Nov. 7, 2013

Related U.S. Application Data

(60) Provisional application No. 61/382,776, filed on Sep. 14, 2010, provisional application No. 61/424,242, filed on Dec. 17, 2010.

(51) Int. Cl.
| | |
|---|---|
| C07C 37/86 | (2006.01) |
| B01J 21/00 | (2006.01) |
| B01J 23/62 | (2006.01) |
| B01J 37/02 | (2006.01) |
| B01J 37/18 | (2006.01) |
| C07C 2/74 | (2006.01) |
| C07C 37/07 | (2006.01) |
| C07C 37/08 | (2006.01) |
| C07C 39/04 | (2006.01) |
| C07C 45/53 | (2006.01) |
| C07C 407/00 | (2006.01) |
| C07C 409/14 | (2006.01) |

(52) U.S. Cl.
CPC .............. *C07C 37/86* (2013.01); *B01J 21/00* (2013.01); *B01J 23/622* (2013.01); *B01J 37/0201* (2013.01); *B01J 37/18* (2013.01); *C07C 2/74* (2013.01); *C07C 37/07* (2013.01); *C07C 37/08* (2013.01); *C07C 39/04* (2013.01); *C07C 45/53* (2013.01); *C07C 407/00* (2013.01); *C07C 409/14* (2013.01); *C07C 2101/14* (2013.01); *C07C 2521/04* (2013.01); *C07C 2521/06* (2013.01); *C07C 2521/08* (2013.01); *C07C 2521/12* (2013.01); *C07C 2521/14* (2013.01); *C07C 2521/16* (2013.01); *C07C 2529/70* (2013.01); *C07C 2529/74* (2013.01); *C07C 2529/76* (2013.01)

(58) Field of Classification Search
CPC .......... C07C 39/04; C07C 2/74; C07C 37/07; C07C 37/08; C07C 37/86; C07C 407/00; C07C 409/14; C07C 45/53; C07C 2101/14; C07C 2521/04; C07C 2521/06; C07C 2521/08; C07C 2521/12; C07C 2521/14; C07C 2521/16; C07C 2529/70; C07C 2529/74; C07C 2529/76; B01J 21/00; B01J 23/622; B01J 37/0201; B01J 37/18
See application file for complete search history.

(56) References Cited

U.S. PATENT DOCUMENTS

| | | | |
|---|---|---|---|
| 3,140,243 A | 7/1964 | Feder et al. | |
| 3,140,318 A | 7/1964 | Sodomann et al. | |
| 3,322,651 A | 5/1967 | Nielsen | |
| 3,442,958 A | 5/1969 | Choo | |
| 3,933,916 A | 1/1976 | Lejeune et al. | |
| 4,021,490 A | 5/1977 | Hudson | |
| 4,328,372 A | 5/1982 | Wu | |
| 5,064,507 A | 11/1991 | O'Donnell et al. | |
| 5,428,075 A * | 6/1995 | Pressman et al. | ............... 521/26 |
| 6,037,513 A | 3/2000 | Chang et al. | |
| 6,388,144 B1 | 5/2002 | Wijesekera et al. | |
| 7,002,048 B2 | 2/2006 | Wijesekera et al. | |
| 7,205,442 B2 | 4/2007 | Payne | |

(Continued)

FOREIGN PATENT DOCUMENTS

WO    2011/096989    8/2011

OTHER PUBLICATIONS

Schmidt, Robert J. *"Industrial Catalytic Processes—Phenol Production,"* Applied Catalysis A: General, 2005, vol. 280, pp. 89-103.

*Primary Examiner* — Paul A Zucker
*Assistant Examiner* — Mark Luderer
(74) *Attorney, Agent, or Firm* — Siwen Chen; Stephen A. Baehl

(57) ABSTRACT

Described herein is a process for producing phenol in which (a) benzene and hydrogen are contacted with a hydroalkylation catalyst under hydroalkylation conditions to produce cyclohexylbenzene; (b) the cyclohexylbenzene is contacted with an oxidation catalyst under oxidation conditions to produce cyclohexylbenzene hydroperoxide; (c) the cyclohexylbenzene hydroperoxide is contacted with a cleavage catalyst under cleavage conditions to produce a cleavage effluent comprising phenol and cyclohexanone; (d) the cyclohexanone is contacted with a dehydrogenation catalyst under dehydrogenation conditions to produce a dehydrogenation effluent having at least a portion of the cyclohexanone and a first contaminant; and (e) the first contaminant is contacted with an acidic material under contaminant treatment conditions to convert at least a portion of the first contaminant into a converted first contaminant. Phenol compositions made from the above-described process are also described herein.

11 Claims, 11 Drawing Sheets

(56) References Cited

U.S. PATENT DOCUMENTS

| | | |
|---|---|---|
| 2003/0163007 A1 | 8/2003 | Dyckman et al. |
| 2004/0158105 A1* | 8/2004 | Payne .......................... 568/810 |
| 2006/0211890 A1 | 9/2006 | Fodor |
| 2007/0032681 A1 | 2/2007 | Walsdorff et al. |
| 2011/0105805 A1 | 5/2011 | Buchanan et al. |
| 2011/0301387 A1 | 12/2011 | Wang et al. |
| 2013/0225871 A1* | 8/2013 | Kuechler et al. .............. 568/716 |

\* cited by examiner

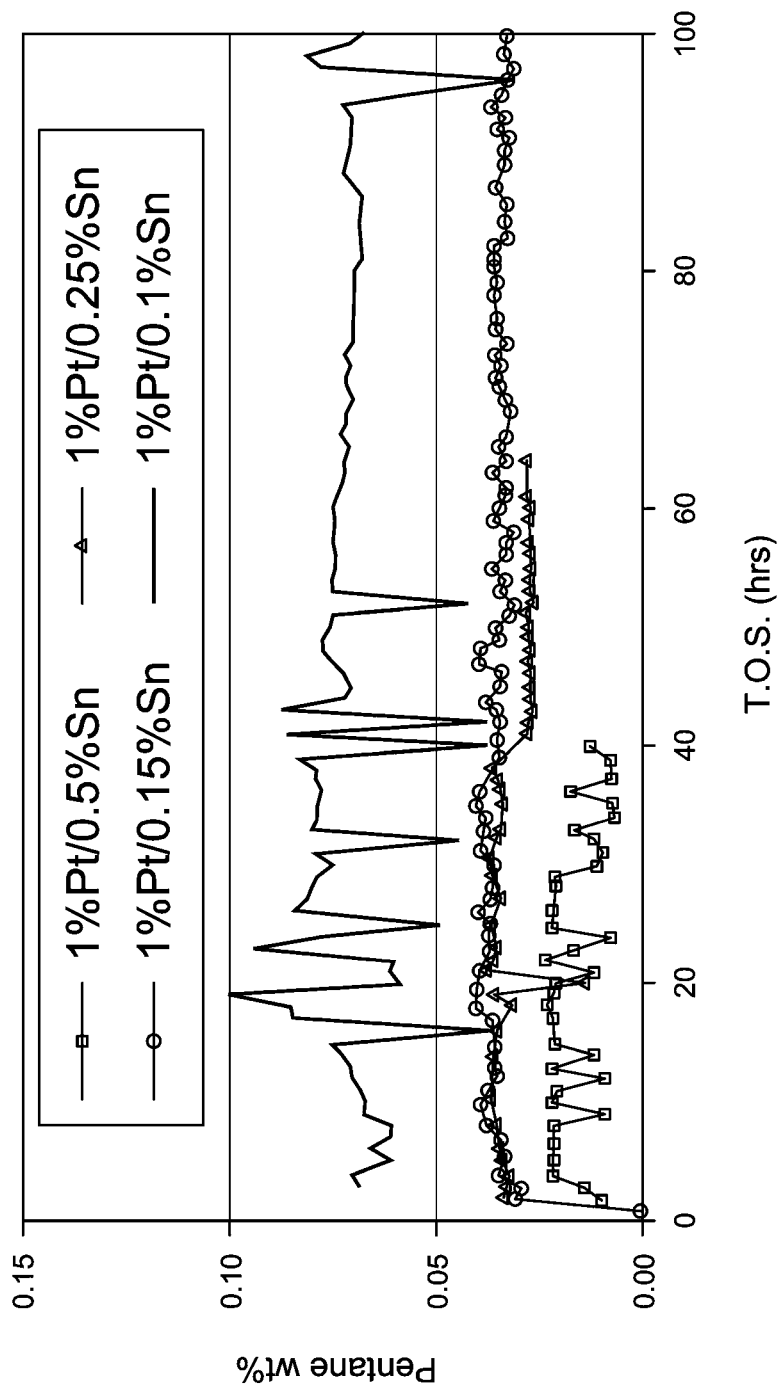

DEHYDROGENATION PROCESSES AND PHENOL COMPOSITIONS

PRIORITY CLAIM

This application is a National Stage Application of International Application No. PCT/US2011/047829 filed Aug. 16, 2011, which claims priority to and the benefit of U.S. Provisional Application Ser. No. 61/424,242, filed on Dec. 17, 2010, and 61/382,776 filed on Sep. 14, 2010, both of which are incorporated herein by reference in their entirety.

FIELD

The present invention relates to methods for dehydrogenating cyclohexanone to produce phenol, and compositions produced from same.

BACKGROUND

Phenol is an important product in the chemical industry and is useful in, for example, the production of phenolic resins, bisphenol A, ε-caprolactam, adipic acid, and plasticizers.

Currently, the most common route for the production of phenol is the Hock process. This is a three-step process in which the first step involves alkylation of benzene with propylene to produce cumene, followed by oxidation of the cumene to the corresponding hydroperoxide and then cleavage of the hydroperoxide to produce equimolar amounts of phenol and acetone.

However, the various steps involved in the production of phenol and acetone from cumene can produce various contaminants that are difficult to separate from the desired phenol and acetone products. Examples of these contaminants may include hydroxyacetone, mesityl oxide, 2-methylbenzofuran, acetophenone, alpha-methylstyrene, cumene, 2-phenylpropanal.

These contaminants, if left in the phenol product, may cause difficulties in downstream processing, or render the phenol unusable for such downstream processing, for example in the subsequent production of bis-phenols and polycarbonates. Therefore, techniques have been proposed to remove those contaminants involving certain treatments. For example, U.S. Pat. No. 5,064,507 discloses obtaining high purity phenol from cleavage of cumene hydroperoxide through one or more amine treatment steps. The phenol mixture includes at least 0.5 wt % to no greater than 10 wt % of alpha-methylstyrene, and further includes acetol, 2-phenylpropionaldehyde (2PPA), methyl-benzofuran (MBF), mesityl oxide (MO) and carbonyl impurities. In addition, U.S. Pat. No. 3,322,651 discloses a method of producing phenol made by decomposition of cumene hydroperoxide. The phenol is purified by contacting the carbonyl compounds with a nitrogen compound.

The production of phenol from cyclohexylbenzene is an emerging technology, interesting in that it co-produces cyclohexanone rather than acetone. Cyclohexylbenzene can be produced, for example, by direct alkylation of benzene with cyclohexene, or as disclosed in U.S. Pat. No. 6,037,513, by contacting benzene with hydrogen in the presence of a catalyst. The cyclohexylbenzene can then be oxidized to the corresponding hydroperoxide and the peroxide cleaved to phenol and cyclohexanone using an acidic cleavage catalyst.

One problem of producing phenol by way of the cleavage of cyclohexylbenzene hydroperoxide is that the cyclohexanone and phenol produce an azeotropic mixture composed of 28 wt % cyclohexanone and 72 wt % phenol. Thus, any attempt to separate the cleavage effluent by simple distillation results in this azeotropic mixture. To obviate this problem it has been proposed to integrate the cyclohexylbenzene oxidation and cleavage process with a dehydrogenation step whereby at least part of the cyclohexanone is converted to additional phenol (see International Patent Publication No. WO2010/024975). Such a dehydrogenation step is generally achieved by contacting the cyclohexanone with a supported metal catalyst at a temperature of about 250° C. to about 500° C.

The production of phenol from cyclohexylbenzene also produces various contaminants that are difficult to separate from the desired products. However, the nature of those contaminants and the separations involved are significantly different than those involved in the conventional Hock process for phenol and acetone. For example, hydroalkylation of benzene produces significant amounts of, inter alia, cyclohexane and lesser amounts of methylcyclopentane, cyclohexene, phenylcyclohexene, and phenylcyclohexyldiene. Similarly, the oxidation of cyclohexylbenzene typically produces peroxide species alien to the Hock process, such as the desired cyclohexyl-1-phenyl-1-hydroperoxide (CHBHP), and undesired byproduct hydroperoxides such as cyclohexyl-1-phenyl-2-hydroperoxide, cyclohexyl-1-phenyl-3-hydroperoxide, and cyclohexyl-1-phenyl-4-hydroperoxide. Similarly, the cleavage of these various hydroperoxides produces, as both the product of the undesired hydroperoxides and the undesired byproducts of the desired CHBHP, a wide variety of contaminant species are not produced by the chemistry and technology of the Hock process. Similarly, the dehydrogenation of cyclohexanone to phenol typically produces various hydrocarbons such as hexanone, cyclohexenol and methylcyclopentenone.

That said, provided herein are methods for producing phenol and cyclohexanone from cyclohexylbenzene and dehydrogenating a portion of the cyclohexanone into phenol. Further described are methods for managing the contaminants that are generated in the above-described process.

Advantageously, the methods described herein produce high-quality phenol compositions that are novel, useful and very different from those typically produced by conventional methods (e.g., the Hock process). The chemistry associated with cyclohexylbenzene as a starting material in the instant invention, and further the complete absence of cumene and its conversion products and byproducts, potentially provides a phenol composition with contaminants that are of a markedly different type and concentration than the conventional methods. These contaminants may be less problematic in further processing, e.g., to phenolic resins. Moreover, the contaminants produced in the processes described herein have lower volatility compared to contaminants produced by conventional methods, and therefore may be present in lower concentrations.

SUMMARY

In one aspect, the invention resides in a process for producing phenol comprising:

(a) contacting benzene and hydrogen with a hydroalkylation catalyst under hydroalkylation conditions to produce cyclohexylbenzene;

(b) contacting at least a portion of the cyclohexylbenzene with an oxidation catalyst under oxidation conditions to produce cyclohexylbenzene hydroperoxide;

(c) contacting at least a portion of the cyclohexylbenzene hydroperoxide with a cleavage catalyst under cleavage conditions to produce a cleavage effluent comprising phenol and cyclohexanone;

(d) contacting at least a portion of the cyclohexanone from the cleavage effluent with a dehydrogenation catalyst under dehydrogenation conditions to produce a dehydrogenation effluent having at least a portion of the cyclohexanone converted to phenol, wherein the dehydrogenation effluent further comprises a first contaminant; and (e) contacting at least a portion of the first contaminant from the dehydrogenation effluent with an acidic material under contaminant treatment conditions to convert at least a portion of the first contaminant into a converted first contaminant.

In another aspect, the invention resides in a composition comprising:

(a) at least 99 wt % phenol; and (b) 0.1 wppm to 1000 wppm of at least one of the following components: bicyclohexane, cyclohexylbenzene, methylcyclopentylbenzene, n-butylbenzene, n-pentylbenzene, pentenylbenzene, hydroxycyclohexanone, cyclohexenone, cyclohexanol, cyclohexanone, cyclohexanedione, benzoic acid, hexanal, methycyclopentanone, hexanone, cyclohexenol and methylcyclopentenone, wherein the wt % and wppm are based upon the total weight of the composition.

In another aspect, the invention resides in a composition comprising:

(a) at least 99.99 wt % phenol;

(b) at least 0.1 wppm to 10 wppm of at least one of bicyclohexane, cyclohexylbenzene, methylcyclopentylbenzene, n-butylbenzene, n-pentylbenzene, and pentenylbenzene; and (c) at least 0.1 wppm to 3 wppm of at least one of: hydroxycyclohexanone, cyclohexenone, cyclohexanol, cyclohexanone, cyclohexanedione, benzoic acid, hexanal, and methycyclopentanone, wherein the wt % and wppm are measured according to ASTM D6142 and are based upon the total weight of the composition, and wherein the total amount of the hydrocarbon components and oxygenate components present in the composition accounts for at least 10 wt % of the total amount of contaminants present in the composition.

BRIEF DESCRIPTION OF THE DRAWINGS

FIG. 11 is a graph comparing pentane production against time on stream for the calcined 1% Pt/x % Sn/SiO$_2$ catalysts of Examples 3 to 8.

DETAILED DESCRIPTION

Figure 1:
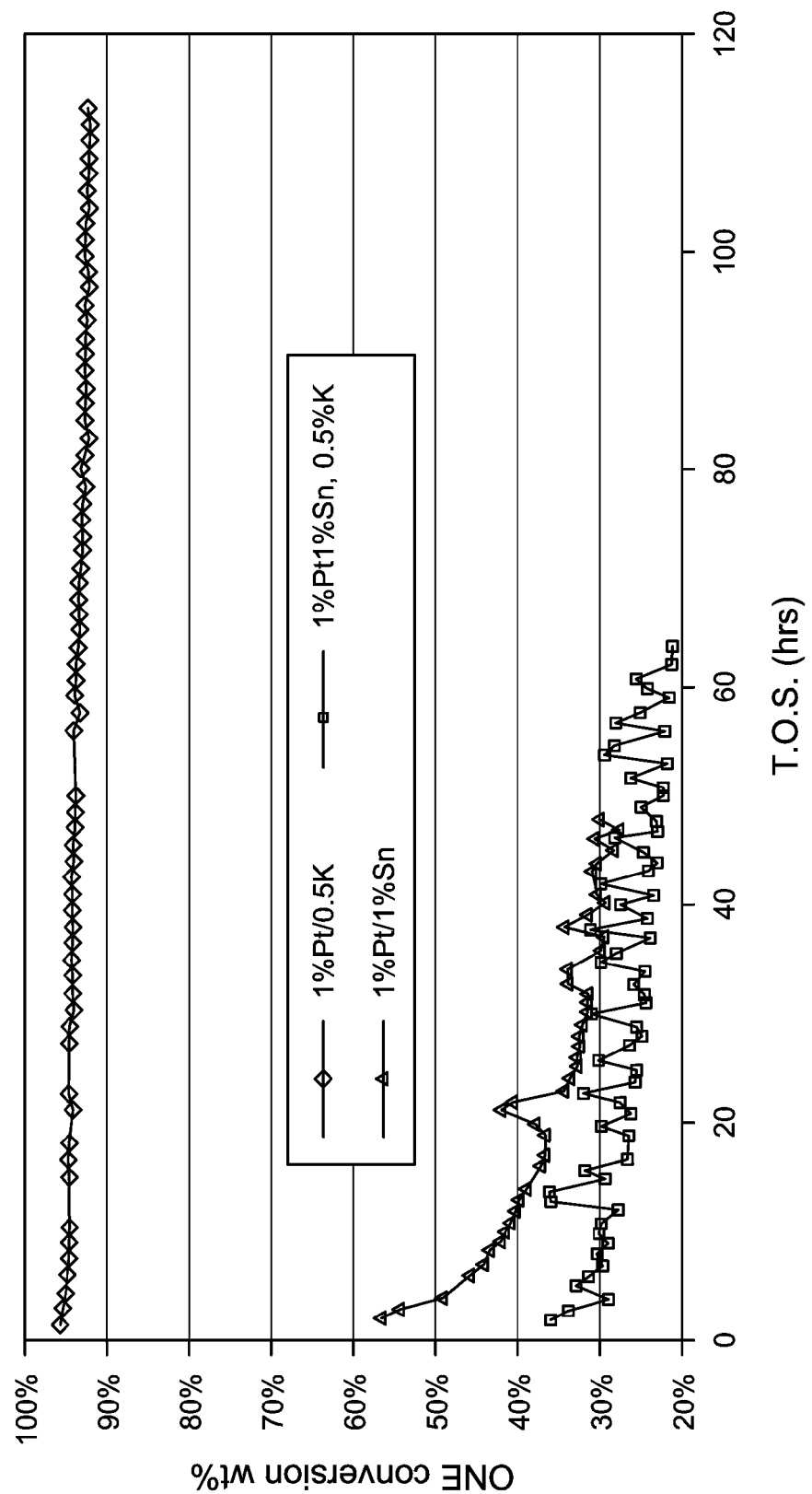
FIG. 1 is a graph comparing cyclohexanone conversion against time on stream for the 1% Pt/1% Sn/SiO$_2$ catalyst of Example 7 and the 1% Pt/1% Sn/0.5% K/SiO$_2$ catalyst of Example 9B with that of the 1% Pt/0.5% K/SiO$_2$ catalyst of Comparative Example 1.

Described herein is a process for producing phenol via cyclohexylbenzene. In this process, benzene is hydroalkylated to produce cyclohexylbenzene, which then undergoes oxidation and cleavage to produce phenol and cyclohexanone. The cyclohexanone is then dehydrogenated to produce additional phenol with hydrogen. The hydrogen is optionally recycled to the benzene hydroalkylation step. In various embodiments, one or more contaminants is generated in the above-described steps and the process further comprises treating at least a portion of the one or more contaminants with an acidic material to convert the contaminant into a converted contaminant which is more easily separated from the mixture.

In various embodiments, the dehydrogenation catalyst is a catalyst composition and a method of its synthesis, in which the catalyst composition comprises (i) a support; (ii) a dehydrogenation component comprising at least one metal or compound thereof selected from Groups 6 to 10 of the Periodic Table of Elements; and (iii) tin or a tin compound present in an amount of about 0.01 wt % to about 0.25 wt % of tin based upon the total weight of the catalyst composition. The catalyst composition is useful in the dehydrogenation of cycloaliphatic alcohols and ketones to the corresponding hydroxyaromatic alcohols and, in particular, in the dehydrogenation of cyclohexanone to produce phenol. However, it will be appreciated that other dehydrogenation catalysts may be used.

Production of Cyclohexylbenzene

In the integrated process for producing phenol and cyclohexanone from benzene, the benzene is initially converted to cyclohexylbenzene by any conventional technique, including alkylation of benzene with cyclohexene in the presence of an acid catalyst, such as zeolite beta or an MCM-22 family molecular sieve, or by oxidative coupling of benzene to make biphenyl followed by hydrogenation of the biphenyl. However, in practice, the cyclohexylbenzene is generally produced by contacting the benzene with hydrogen under hydroalkylation conditions in the presence of a hydroalkyla tion catalyst whereby the benzene undergoes the following reaction (1) to produce cyclohexylbenzene (CHB):

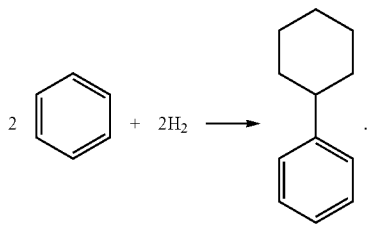

(1)

For an example of hydroalkylation of benzene in the presence of hydrogen for the production of cyclohexylbenzene, see U.S. Pat. Nos. 6,730,625 and 7,579,511 which are incorporated by reference. Also, see International Applications WO2009131769 or WO2009128984 directed to catalytic hydroalkylation of benzene in the presence of hydrogen for the production of cyclohexylbenzene.

Any commercially available benzene feed can be used in the hydroalkylation reaction, but preferably the benzene has a purity level of at least 99 wt %. Similarly, although the source of hydrogen is not critical, it is generally desirable that the hydrogen is at least 99 wt % pure.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 kPa and about 7,000 kPa, such as between about 500 kPa and about 5,000 kPa. Suitable values for the molar ratio of hydrogen to benzene are between about 0.15:1 and about 15:1, such as between about 0.4:1 and about 4:1 for example between about 0.4 and about 0.9:1.

The catalyst employed in the hydroalkylation reaction is a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes molecular sieves having the MWW framework topology. (Such crystal structures are discussed in the "Atlas of Zeolite Framework Types", Fifth edition, 2001, the entire content of which is incorporated as reference.)

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49; (b) MCM-56; and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 wt % and about 10 wt %, such as between about 0.1 wt % and about 5 wt %, of the catalyst.

Suitable binder materials include synthetic or naturally occurring substances as well as inorganic materials such as clay, silica, and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia, and Florida clays or others in which the main mineral constituent is halloysite, kaolinite, dickite, nacrite, or anauxite. Such clays can be used in the raw state as originally mined or initially subjected to calcination, acid treatment, or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Although the hydroalkylation reaction is highly selective towards cyclohexylbenzene, the effluent from the hydroalkylation reaction may contain some dialkylated products, as well as unreacted benzene and the desired monoalkylated species. The unreacted benzene may be recovered by distillation and recycled to the alkylation reactor. The bottoms from the benzene distillation are further distilled to separate the monocyclohexylbenzene product from any dicyclohexylbenzene and other heavies. Depending on the amount of dicyclohexylbenzene present in the reaction effluent, it may be desirable to either (a) transalkylate the dicyclohexylbenzene with additional benzene or (b) dealkylate the dicyclohexylbenzene to maximize the production of the desired monoalkylated species.

Transalkylation with additional benzene is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y, zeolite USY, and mordenite. The transalkylation reaction is typically conducted under at least partial liquid phase conditions, which suitably include a temperature of about 100° C. to about 300° C., a pressure of about 800 kPa to about 3500 kPa, a weight hourly space velocity of about 1 $hr^{-1}$ to about 10 $hr^{-1}$ on total feed, and a benzene/dicyclohexylbenzene weight ratio about of 1:1 to about 5:1.

One by-product of the hydroalkylation reaction is cyclohexane. Although a $C_6$-rich stream comprising cyclohexane and unreacted benzene can be readily removed from the hydroalkylation reaction effluent by distillation, owing to the similarity in the boiling points of benzene and cyclohexane, the $C_6$-rich stream is difficult to further separate by simple distillation. However, some or all of the $C_6$-rich stream can be recycled to the hydroalkylation reactor to provide not only part of the benzene feed but also part of the diluents mentioned above.

In some cases, it may be desirable to supply some of the $C_6$-rich stream to a dehydrogenation reaction zone, where the $C_6$-rich stream is contacted with a dehydrogenation catalyst under dehydrogenation conditions sufficient to convert at least part of the cyclohexane in the $C_6$-rich stream portion to benzene, which again can be recycled to the hydroalkylation reaction. The dehydrogenation catalyst generally comprises (a) a support; (b) a hydrogenation-dehydrogenation component; and (c) an inorganic promoter. Conveniently, the support (a) is selected from the group consisting of silica, a silicate, an aluminosilicate, zirconia, and carbon nanotubes, and preferably comprises silica. Suitable hydrogenation-dehydrogenation components (b) comprise at least one metal selected from Groups 6 to 10 of the Periodic Table of Elements, such as platinum, palladium and compounds and mixtures thereof. Typically, the hydrogenation-dehydrogenation component is present in an amount between about 0.1 wt % and about 10 wt % of the catalyst. A suitable inorganic promoter (c) comprises at least one metal or compound thereof selected from Group 1 of the Periodic Table of Elements, such as a tin compound. Typically, the promoter is present in an amount between about 0.1 wt % and about 5 wt % of the catalyst. Suitable dehydrogenation conditions include a temperature of about 250° C. to about 500° C., a pressure of about atmospheric to about 500 psig (100 kPa to 3550 kPa), a weight hourly space velocity of about 0.2 $hr^{-1}$ to 50 $hr^{-1}$, and a hydrogen to hydrocarbon feed molar ratio of about 0 to about 20. As used herein, the numbering scheme for the Periodic Table Groups is as disclosed in Chemical and Engineering News, 63(5), 27 (1985).

After removal of the unreacted benzene and the polyalkylated benzenes and other heavy species, the cyclohexylbenzene is fed to the oxidation reaction. Typically, however, this cyclohexylbenzene composition (also referred to as cyclohexylbenzene feed) contains the following contaminants generated as by-products of its synthesis:

between 1 wppm and 1 wt % bicyclohexane, or between 10 wppm and 8000 wppm bicyclohexane;

between 1 wppm and 1 wt % biphenyl, or between 10 wppm and 8000 wppm biphenyl;

between 1 wppm and 2 wt % methylcyclopentylbenzene, or between 10 wppm and 1 wt % methylcyclopentylbenzene as any isomer: 1-phenyl-1-methylcyclopentane, 1-phenyl-2-methylcyclopentane, and 1-phenyl-3-methylcyclopentane; and less than about 1000 wppm, such as less than 100 wppm of phenol, olefins or alkylene benzenes, such as cyclohexenyl benzene.

Cyclohexylbenzene Oxidation

In order to convert the cyclohexylbenzene into phenol and cyclohexanone, cyclohexylbenzene (such as part of a cyclohexylbenzene composition) is oxidized to the corresponding hydroperoxide. This is accomplished by contacting the cyclohexylbenzene with oxygen (e.g., an oxygen-containing gas, such as air and various derivatives of air). For example, it is possible to use air that has been compressed and filtered to removed particulates, air that has been compressed and cooled to condense and remove water, or air that has been enriched in oxygen above the natural approximately 21 mol % in air through membrane enrichment of air, cryogenic separation of air or other conventional means.

The oxidation is conducted in the presence of a catalyst. Suitable oxidation catalysts include N-hydroxy substituted cyclic imides described in U.S. Pat. No. 6,720,462, which is incorporated herein by reference for this purpose. For example, N-hydroxyphthalimide (NHPI), 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt, or N-hydroxy-o-benzenedisulphonimide may be used. Preferably, the catalyst is N-hydroxyphthalimide. Another suitable catalyst is N,N',N"-thihydroxyisocyanuric acid.

These oxidation catalysts can be used either alone or in conjunction with a free radical initiator, and further can be used as liquid-phase, homogeneous catalysts or can be supported on a solid carrier to provide a heterogeneous catalyst. Typically, the N-hydroxy substituted cyclic imide or the N,N', N"-trihydroxyisocyanuric acid is employed in an amount between 0.0001 wt % to 15 wt %, such as between 0.001 wt % to 5 wt %, of the cyclohexylbenzene.

Suitable conditions for the oxidation step include a temperature between about 70° C. and about 200° C., such as about 90° C. to about 130° C., and a pressure of about 50 kPa to 10,000 kPa. A basic buffering agent may be added to react with acidic by-products that may form during the oxidation. In addition, an aqueous phase may be introduced. The reaction can take place in a batch or continuous flow fashion.

The reactor used for the oxidation reaction may be any type of reactor that allows for introduction of oxygen to cyclohexylbenzene, and may further efficaciously provide contacting of oxygen and cyclohexylbenzene to effect the oxidation reaction. For example, the oxidation reactor may comprise a simple, largely open vessel with a distributor inlet for the oxygen-containing stream. In various embodiments, the oxidation reactor may have means to withdraw and pump a portion of its contents through a suitable cooling device and return the cooled portion to the reactor, thereby managing the exothermicity of the oxidation reaction. Alternatively, cooling coils providing indirect cooling, say by cooling water, may be operated within the oxidation reactor to remove the generated heat. In other embodiments, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner.

Typically, the product of the cyclohexylbenzene oxidation reaction (also referred to as an oxidation effluent) contains at least 5 wt %, such as at least 10 wt %, for example at least 15 wt %, or at least 20 wt % cyclohexyl-1-phenyl-1-hydroperoxide based upon the total weight of the oxidation effluent. Generally, the oxidation effluent contains no greater than 80 wt %, or no greater than 60 wt %, or no greater than 40 wt %, or no greater than 30 wt %, or no greater than 25 wt % of cyclohexyl-1-phenyl-1-hydroperoxide based upon the total weight of the oxidation effluent. The oxidation effluent may further comprise imide catalyst and unreacted cyclohexylbenzene. For example, the oxidation effluent may include unreacted cyclohexylbenzene in an amount of at least 50 wt %, or at least 60 wt %, or at least 65 wt %, or at least 70 wt %, or at least 80 wt %, or at least 90 wt %, based upon total weight of the oxidation effluent.

At least a portion of the oxidation effluent is subjected to a cleavage reaction to convert the cyclohexyl-1-phenyl-1-hydroperoxide to phenol and cyclohexanone. Cleavage may be conducted on oxidation effluent, with or without the effluent undergoing any prior separation or treatment. For example, all or a fraction of the oxidation effluent may be subjected to high vacuum distillation to generate a product enriched in unreacted cyclohexylbenzene and leave a residue which is concentrated in the desired cyclohexyl-1-phenyl-1-hydroperoxide and which is subjected to the cleavage reaction. In general, however, such concentration of the cyclohexyl-1-phenyl-1-hydroperoxide is neither necessary nor preferred. Additionally or alternatively, all or a fraction of the oxidation effluent, or all or a fraction of the vacuum distillation residue may be cooled to cause crystallization of the unreacted imide oxidation catalyst, which can then be separated either by filtration or by scraping from a heat exchanger surface used to effect the crystallization. At least a portion of the resultant oxidation effluent reduced or free from imide oxidation catalyst may be subjected to the cleavage reaction.

As another example, all or a fraction of the oxidation effluent may be subjected to water washing and then passage through an adsorbent, such as a 3 A molecular sieve, to separate water and other adsorbable compounds, and provide an oxidation effluent with reduced water or imide content that may be subjected to the cleavage reaction. Similarly, all or a fraction of the oxidation effluent may undergo a chemically or physically based adsorption, such as passage over a bed of sodium carbonate to remove the imide oxidation catalyst (e.g., NHPI) or other adsorbable components, and provide an oxidation effluent reduced in oxidation catalyst or other adsorbable component content that may be subjected to the cleavage reaction. Another possible separation involves contacting all or a fraction of the oxidation effluent with a liquid containing a base, such as an aqueous solution of an alkali metal carbonate or hydrogen carbonate, to form an aqueous phase comprising a salt of the imide oxidation catalyst, and an organic phase reduced in imide oxidation catalyst. An example of separation by basic material treatment is disclosed in International Application No. WO 2009/025939.

Hydroperoxide Cleavage

Another reactive step in the conversion of the cyclohexylbenzene into phenol and cyclohexanone involves the acid-catalyzed cleavage of the cyclohexyl-1-phenyl-1-hydroperoxide produced in the oxidation step.

Generally, the acid catalyst used in the cleavage reaction is at least partially soluble in the product of the cleavage reaction (also referred to as the cleavage effluent), is stable at a temperature of at least 185° C. and has a lower volatility (higher normal boiling point) than cyclohexylbenzene. Typically, the acid catalyst is also at least partially soluble in the cleavage effluent. Suitable acid catalysts include, but are not limited to, Brønsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, and sulfur trioxide. Sulfuric acid is a preferred acid catalyst.

In various embodiments, the cleavage effluent contains at least 50 weight-parts-per-million (wppm) and no greater than 5000 wppm of the acid catalyst, or at least 100 wppm to and to no greater than 3000 wppm, or at least 150 wppm to and no greater than 2000 wppm of the acid catalyst, or at least 300 wppm and no greater than 1500 wppm of the acid catalyst, based upon total weight of the cleavage effluent.

In one embodiment, the cleavage effluent contains a polar solvent, such as an alcohol containing less than 6 carbons, such as methanol, ethanol, iso-propanol, and/or ethylene glycol; a nitrile, such as acetonitrile and/or propionitrile; nitromethane; and a ketone containing 6 carbons or less such as acetone, methylethyl ketone, 2- or 3-pentanone, cyclohexanone, and methylcyclopentanone. The preferred polar solvent is acetone. Generally, the polar solvent is added to the cleavage effluent such that the weight ratio of the polar solvent to the cyclohexylbenzene hydroperoxide in the mixture is in the range of about 1:100 to about 100:1, such as about 1:20 to about 10:1, and the mixture comprises about 10 wt % to about 40 wt % of the cyclohexylbenzene hydroperoxide. The addition of the polar solvent is found not only to increase the degree of conversion of the cyclohexylbenzene hydroperoxide in the cleavage reaction but also to increase the selectivity of the conversion to phenol and cyclohexanone. Although the mechanism is not fully understood, it is believed that the polar solvent reduces the free radical inducted conversion of the cyclohexylbenzene hydroperoxide to undesired products such as hexanophenone and phenylcyclohexanol.

In various embodiments, the cleavage effluent includes cyclohexylbenzene in an amount of at least 50 wt %, or at least 60 wt %, or at least 65 wt %, or at least 70 wt %, or at least 80 wt %, or at least 90 wt %, based upon total weight of the cleavage effluent.

Suitable cleavage conditions include a temperature of greater than 50° C. and no greater than 200° C., or at least 55° C. and no greater than 120° C., and a pressure of at least 1 psig and no greater than 370 psig (at least 7 kPa, gauge and no greater than 2,550 kPa, gauge), or at least 14.5 psig and no greater than 145 psig (at least 100 kPa, gauge and no greater than 1,000 kPa, gauge) such that the cleavage effluent is completely or predominantly in the liquid phase during the cleavage reaction.

The reactor used to effect the cleavage reaction may be any type of reactor known to those skilled in the art. For example, the cleavage reactor may be a simple, largely open vessel operating in a near-continuous stirred tank reactor mode, or a simple, open length of pipe operating in a near-plug flow reactor mode. In other embodiments, the cleavage reactor comprises a plurality of reactors in series, each performing a portion of the conversion reaction, optionally operating in different modes and at different conditions selected to enhance the cleavage reaction at the pertinent conversion range. In one embodiment, the cleavage reactor is a catalytic distillation unit.

In various embodiments, the cleavage reactor is operable to transport a portion of the contents through a cooling device and return the cooled portion to the cleavage reactor, thereby managing the exothermicity of the cleavage reaction. Alternatively, the reactor may be operated adiabatically. In one embodiment, cooling coils operating within the cleavage reactor(s) remove any heat generated.

The major products of the cleavage reaction of cyclohexyl-1-phenyl-1-hydroperoxide are phenol and cyclohexanone, each of which generally comprise about 40 wt % to about 60 wt %, or about 45 wt % to about 55 wt % of the cleavage reaction effluent, such wt % based on the weight of the cleavage effluent exclusive of unreacted cyclohexylbenzene and acid catalyst.

The cleavage effluent also typically contains unreacted acid catalyst and hence at least a portion of the cleavage effluent may be neutralized with a basic material to remove or reduce the level of acid in the product.

Suitable basic materials include alkali metal hydroxides and oxides, alkali earth metal hydroxides and oxides, such as sodium hydroxide, potassium hydroxide, magnesium hydroxide, calcium hydroxide, calcium oxide, and barium hydroxide. Sodium and potassium carbonates may also be used, optionally at elevated temperatures.

In various embodiments, the basic material comprises one or more of: a caustic exchange resin (e.g., sulfonic ion-exchange resin); ammonia or ammonium hydroxide; a basic clay such as limestone, dolomite, magnesite, sepiolite, and olivine; an activated carbon and/or impregnated activated carbon; an anionic exchange resin, such as a weakly basic ion exchange resin having a styrene-divinyl benzene polymer backbone and an amine functional structure selected from —N(CH$_3$)$_2$, —NRH or —NR$_2$, where R is a hydrogen or an alkyl group containing 1 to 20 carbon atoms; an amine polysiloxane functionalized with ethylenediamine; an organic basic material grafted on microporous or mesoporous metal oxides; other organo-inorganic solids, such as zeolites exchanged with a metal selected from the group of lithium, sodium potassium, rubidium, cesium, calcium, barium, strontium, and radium; an oxide of Group III of the Periodic Table of Elements treated with a metal selected from lithium, potassium, sodium, rubidium, and cesium; a supported or solid alkali, alkaline-earth metal or organometallic; a magnesium silicate generally derived from the interaction of a magnesium salt and soluble silicate; a salt with basic hydrolysis such as sodium acetate, sodium bicarbonate, sodium phenate, and sodium carbonate; and amine(s), such as a primary, secondary, or tertiary aliphatic amines or aromatic amines, e.g., anilines, n-butyl amine, heterocyclic amines, such as pyridines, piperidines, piperazines, tri-ethyl amine, aliphatic or aromatic diamines and alkanolamines. In particular, amines in the form of their salts with weak organic acids may be used. Conveniently, the basic material is a diamine, such as 2-methylpentamethyenediamine or hexamethylenediamine, which are commercially available from Invista S.à r.l. Corporation under the trade designations DYTEK™ A and DYTEK™ HMD.

Suitable solid basic materials include: basic metal oxide families; alkali on metal oxides; alkaline-earth on metal oxides; alkali and alkaline-earth zeolites; transition metals, rare earth and higher valence oxides; hydrotalcites, calcined hydrotalcites and spinels, specifically hydrotalcites treated with an alkali metal selected from lithium, potassium, sodium, rubidium, cesium, and combinations thereof; perovskites; and beta-aluminas.

In one embodiment, the basic material is one or more of the hindered amines described in U.S. Pat. No. 6,201,157. It will be understood that the basic material may be added in the anhydrous state or may be an aqueous solution of any of the foregoing basic materials, particularly the metal hydroxides and salts with basic hydrolysis.

Conveniently, a liquid basic material employed a neutralization reaction in the present invention, such as an amine or diamine as has been discussed, has a relatively low volatility, with a normal boiling point temperature above that of cyclohexylbenzene, such that it will tend to remain in the bottoms product in subsequent fractionation operations that may be conducted on the least a portion of the treated cleavage effluent that may contain such liquid basic material.

The conditions at which the neutralization reaction is effected vary with the acid catalyst and basic material employed. Suitable neutralization conditions include a temperature of at least 30° C., or at least 40° C., or at least 50° C., or at least 60° C., or at least 70° C., or at least 80° C., or at least 90° C. Other suitable neutralization conditions include a temperature of no greater than 200° C., or no greater than 190° C., or no greater than 180° C., or no greater than 170° C., or no greater than 160° C., or no greater than 150° C., or no greater than 140° C., or no greater than 130° C., or no greater than 120° C., or no greater than 110° C., or no greater than 100° C. In various embodiments, the neutralization conditions include a temperature that is reduced from cleavage reaction conditions, for example, the temperature may be 1° C., or 5° C., or 10° C., or 15° C., or 20° C., or 30° C., or 40° C. lower than the temperature of the cleavage reaction.

Suitable neutralization conditions may include a pressure of about 1 psig to about 500 psig (5 kPa to 3450 kPa, gauge), or about 10 psig to 200 psig (70 kPa, gauge to 1380 kPa, gauge) such that the treated cleavage effluent is completely or predominantly in the liquid phase during the neutralization reaction.

After neutralization, the neutralized acid product can be removed from the cleavage product leaving a crude mixture of phenol and cyclohexanone which is then treated to convert at least part of the cyclohexanone to additional phenol.

Cleavage Effluent

In various embodiments, the cleavage effluent further comprises at least 0.1 wt % and no greater than 10 wt %, or at least 0.5 wt % and no greater than 7 wt %, or at least 1 wt % and no greater than 5 wt %, or at least 1.5 wt % and no greater than 3 wt % of any one or combination of contaminant byproducts based on the total weight of the cleavage effluent.

As used herein, a "contaminant" or a "contaminant byproduct" may include any unwanted hydrocarbon or oxygenated hydrocarbon component in the cleavage effluent or the neturalized cleavage effluent, or any portion of either; that is anything other than phenol, cyclohexanone and cyclohexylbenzene. They are unwanted because their presence indicates a decreased yield of desired product phenol and cyclohexanone from cyclohexylbenzene, or they cause difficulties in the separation and purification of phenol, cyclohexanone or unconverted cyclohexylbenzene, or some combination thereof. A contaminant in the cleavage effluent or the neturalized cleavage effluent or any portion thereof may have been produced in any element of the present invention, or may have been contained in the feed comprising cyclohexylbenzene undergoing oxidation. For example, a contaminant may be present in the cleavage effluent as a result of one or more of: (i) it was included with the cyclohexylbenzene (e.g., as a byproduct of production using hydroalkylation or alkylation); (ii) it was produced in oxidation of the feed comprising cyclohexylbenzene, and potentially the oxidation of an oxidizable component from (i); and/or (iii) it was produced in the cleavage reaction of at least a portion of the oxidation effluent from (ii).

Examples of contaminants in the cleavage effluent, and possible amounts thereof, include (weight-parts-per-million (wppm) and wt % are based upon total weight of the cleavage effluent):

water, e.g., at least 100 wppm and no greater than 3.0 wt %;

twelve carbon, two ringed hydrocarbons other than cyclohexylbenzene, such as bicyclohexane, cyclohexenylcyclohexane, and cyclohexadienylcyclohexane, cyclohexenylbenzene, cyclohexadienylbenzene and biphenyl, e.g., at least 10 wppm and no greater than 3.0 wt %, each or in total;

saturated and unsaturated ketones, such as pentanones, methylcyclopentanones, hexanones, 1-phenylhexan-1-one and 1-cyclohexylhexan-1-one, phenylcyclohexanones and phenylmethylcyclopentanones, e.g., at least 10 wppm and no greater than 4.0 wt %, each or in total;

cyclohexyldione(s), e.g., at least 10 wppm and no greater than 1.0 wt % in total;

less than 12 carbon, unsaturated hydrocarbons, cyclic and acyclic, or combinations thereof, such as cyclohexene, e.g., at least 10 wppm and no greater than 1.0 wt %, each or in total;

cyclohexanol, e.g., at least 10 wppm and no greater than 1.0 wt %;

cyclohexenone(s), e.g., 2-cyclohexenone or 3-cyclohexenone, e.g., at least 10 wppm and no greater than 2.0 wt %, each or in total;
hydroxycyclohexanone(s), e.g., at least 10 wppm and no greater than 2.0 wt % in total;
carboxylic acids, such as benzoic acid, e.g., at least 10 wppm and no greater than 1.0 wt %, each or in total;
phenyl cyclohexanol(s), e.g., 1-phenylcyclohexan-1-ol, 2-phenylcyclohexan-1-ol, 3-phenylcyclohexan-1-ol and 4-phenylcyclohexan-1-ol, e.g., at least about 10 wppm and no greater than 5.0 wt %, each or in total;
cyclohexyl cyclohexanol(s), such as 1-cyclohexylcyclohexan-1-ol, 2-cyclohexylcyclohexan-1-ol, 3-cyclohexylcyclohexan-1-ol, and 4-cyclohexylcyclohexan-1-ol, e.g., at least 10 wppm and no greater than 1.0 wt %, each or in total;
unsaturated alkyl oxygenated cyclohexanes, such as cyclohexenyl cyclohexanols and cyclohexenyl cyclohexanones, and methylcyclopentenyl cyclohexanols and methylcyclopentenyl cyclohexanones, e.g., at least 10 wppm and no greater than 1.0 wt %, each or in total;
aldehydes, especially, pentanals, hexanals, cyclohexyl or methylcyclopentyl alkyl aldehydes, such 5-cyclohexyl hexanal, and 6-hydroxy-5-cyclohexyl hexanal, e.g., at least 10 wppm and no greater than 1.0 wt %, each or in total;
1-phenyl-6-hydroxyhexan-1-one (also called 6-hydroxyhexanophenone), e.g., at least 10 wppm and no greater than 4.0 wt %;
1-cyclohexyl-6-hydroxyhexan-1-one, e.g., at least 10 wppm and no greater than 1.0 wt %;
benzoic esters, e.g., at least 10 wppm and no greater than 1.0 wt %, each or in total; and
a hydroperoxide (e.g., an unreacted hydroperoxide). Non-limiting examples include: the desired cyclohexyl-1-phenyl-1-hydroperoxide, and the other hydroperoxides such as cyclohexyl-1-phenyl-2-hydroperoxide, cyclohexyl-1-phenyl-3-hydroperoxide, cyclohexyl-1-phenyl-4-hydroperoxide, cyclopentyl-1-methyl-2-phenyl-2-hydroperoxide, cyclopentyl-1-methyl-3-phenyl-3-hydroperoxide, cyclopentyl-1-methyl-1-phenyl-2-hydroperoxide, cyclopentyl-1-methyl-1-phenyl-3-hydroperoxide, cyclohexyl-1-phenyl-1,2-dihydroperoxide, cyclohexyl-1-phenyl-1,3-dihydroperoxide, cyclohexyl-1-phenyl-1,4-dihydroperoxide; cyclopentyl-1-methyl-2-phenyl-1,2-dihydroperoxide, cyclopentyl-1-methyl-2-phenyl-2,3-dihydroperoxide, cyclopentyl-1-methyl-2-phenyl-2,4-dihydroperoxide, and cyclopentyl-1-methyl-2-phenyl-2,5-dihydroperoxide; e.g., at least 1 wppm and no greater than 1.0 wt %, each or in total.

Cyclohexanone Dehydrogenation

In order to maximize the production of phenol from the benzene starting material, at least part of the cyclohexanone in the cleavage effluent may be subjected to dehydrogenation to form a dehydrogenation effluent according to the following reaction:

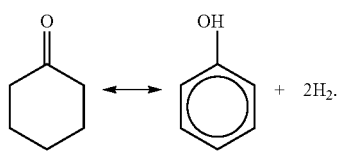

As stated above, cyclohexanone and phenol produce an azeotropic mixture composed of 28 wt % cyclohexanone and 72 wt % phenol, so that any attempt to separate the effluent from the cyclohexylbenzene hydroperoxide cleavage step by simple distillation results in this azeotropic mixture. Moreover, although the efficiency of the separation can be enhanced by conducting the distillation under at least partial vacuum, phenol/cyclohexanone separation remains a costly process. Thus, in one embodiment, the feed to the dehydrogenation step has the same composition as the cleavage effluent, thereby avoiding the need for an initial expensive separation step. Depending on the efficiency of the cyclohexanone dehydrogenation, the final product may contain substantially all phenol, thereby at least reducing the problem of separating the phenol from the cleavage effluent.

In another embodiment, the cleavage effluent is subjected to one or more separation processes to recover or remove one or more components of the effluent prior to dehydrogenation. In one embodiment, the cleavage effluent may be separated into a phenol-rich stream and a cyclohexanone-rich stream. For example, the cleavage effluent may be conveniently subjected to at least a first separation step to recover some or all of the phenol from the effluent, typically so that the effluent stream fed to said dehydrogenation reaction contains less than 50 wt %, for example less than 30 wt %, such as less than 1 wt %, phenol. The separation of phenol is conveniently effected by vacuum and/or extractive distillation. Additional distillation steps can be used to remove components boiling below 155° C. (as measured at 101 kPa), such as benzene and cyclohexene, and/or components boiling above 185° C. (as measured at 101 kPa), such as 2-phenyl phenol and diphenyl ether, prior to feeding the effluent stream to the dehydrogenation reaction.

Any known or hereinafter devised dehydrogenation catalyst may be used in connection with the processes described herein.

In one embodiment, the catalyst employed in the cyclohexanone dehydrogenation reaction comprises (i) a support; (ii) a dehydrogenation component comprising at least one metal or compound thereof selected from Groups 6 to 10 of the Periodic Table of Elements; and (iii) tin or a tin compound. Examples 1-12 and FIGS. 1-11 below illustrate use of such dehydrogenation catalysts.

The tin or tin compound may be present in an amount of greater than about 0.01 wt % to about 0.25 wt %, or about 0.02 wt % to about 0.25 wt %, or about 0.03 wt % to about 0.25 wt %, or about 0.04 wt % to about 0.20 wt %, or about 0.05 wt % to about 0.20 wt %, or about 0.05 wt % to about 0.15 wt %, 0.07 wt % to about 0.1 wt % of tin based upon the total weight of the catalyst composition, with ranges from any lower limit to any upper limit being contemplated. In other embodiments, the tin or tin compound may be replaced by another metal component selected from Group 14 of the Periodic Table of Elements.

It will be understood that the tin in the catalyst composition may not be purely the elemental metal, but could, for example, be at least partly in another form, such as a salt, oxide, chloride, hydride, sulfide, carbonate, etc. For purposes of this application, the wt % of tin or tin compound in the catalyst composition is calculated based upon the amount of tin used to form the catalyst composition. For purposes of illustration, a catalyst composition made with 1.9 grams of tin chloride salt (1 gram of tin) and 22.29 grams of tetraammine platinum hydroxide solution (4.486 wt % Pt) that is supported on 98 grams of silicon dioxide contains 1 wt % of tin and 1 wt % Pt, based upon total weight of the catalyst composition.

Moreover, for purposes of determining wt % s of various components, only that portion of the support that supports the dehydrogenation component and/or the tin or tin compound shall be considered.

The catalyst support is typically formed of silica, a silicate, an aluminosilicate, carbon (e.g., carbon nanotubes). In one embodiment, the support comprises a crystalline, mesoporous silicate material selected from MCM-41, MCM-48 and MCM-50. In other embodiments, the silica support has a surface area as measured by ASTM D3663 in the range from about 10 m$^2$/gram to about 1000 m$^2$/gram, such as from about 20 m$^2$/gram, to about 500 m$^2$/gram, a pore volume in the range of from about 0.2 cc/gram to about 3.0 cc/gram and a median pore diameter in the range from about 10 angstroms to about 2000 angstroms, such as from about 20 angstroms to about 500 angstrom. Such pore volume and median pore diameter values are determined by mercury intrusion porosimetry as described in ASTM D4284. The support may or may not comprise a binder. Suitable silica supports are described in, for example, PCT Pub. No. WO/2007084440A1 filed on Jan. 12, 2007 and entitled "Silica Carriers" and is hereby incorporated by reference for this purpose.

Generally, the dehydrogenation component comprises at least one metal component selected from Groups 6 to 10 of the Periodic Table of Elements, such as platinum (Pt) and/or palladium (Pd). Typically, the dehydrogenation component is present in an amount between about 0.1 wt % and about 10 wt % of the catalyst. In one embodiment, the dehydrogenation component is present in an amount between about 0.1 wt % and about 5 wt % of the catalyst or between about 0.2 wt % and about 4 wt % of the catalyst or between about 0.3 wt % and about 3 wt % of the catalyst or between about 0.4 wt % and 2 wt % of the catalyst.

In one embodiment, the catalyst further contains an inorganic base component comprising a metal component selected from an alkali metal, an alkaline earth metal, an alkali metal compound, and an alkaline earth metal compound, especially potassium or a potassium compound. Typically, the inorganic base component is present in an amount between about 0.1 wt % and about 5 wt %, such as between about 0.1 wt % and about 3 wt %, for example between about 0.1 wt % and about 2 wt %, of the catalyst.

The dehydrogenation catalyst is typically prepared by sequentially or simultaneously treating the support, such as by impregnation, with one or more liquid compositions comprising the dehydrogenation component or a precursor thereof, the tin component or a precursor thereof and/or the optional inorganic base component or a precursor in a liquid carrier, such as water. An organic dispersant may be added to each liquid carrier to assist in uniform application of the metal component(s) to the support. Suitable organic dispersants include amino alcohols and amino acids, such as arginine. Generally, the organic dispersant is present in the liquid composition in an amount between about 1 wt % and about 20 wt % of the liquid composition.

In one preferred embodiment, the catalyst is prepared by sequential impregnation with the tin component being applied to the support before the dehydrogenation component.

After treatment with the liquid composition, the support is heated in one or more stages, generally at a temperature of about 100° C. to about 700° C. for a time of about 0.5 to about 50 hours, to effect one or more of (a) removal of the liquid carrier; (b) conversion of a metal component to a catalytically active form; and (c) decompose the organic dispersant. The heating may be conducted in an oxidizing atmosphere, such as air, or under reducing atmosphere conditions, such as hydrogen. After treatment with a liquid composition containing the dehydrogenation component, the support is generally heated at a temperature of about 200° C. to about 500° C., such as about 300° C. to about 450° C., for a time of about 1 hour to about 10 hours.

In one embodiment, the dehydrogenation catalyst has an oxygen chemisorption value of greater than about 30%, such as greater than about 40%, for example greater than about 50%, even greater than about 60%, greater than about 70%, or even greater than about 80%. As used herein, the oxygen chemisorption value of a particular catalyst is a measure of metal dispersion on the catalyst and is defined as [the ratio of the number of moles of atomic oxygen sorbed by the catalyst to the number of moles of dehydrogenation metal contained by the catalyst]*100%. The oxygen chemisorption values referred to herein are measured using the following technique. Oxygen chemisorption measurements are obtained using the Micromeritics ASAP 2010. Approximately 0.3 to 0.5 grams of catalyst are placed in the Micrometrics device. Under flowing helium, the catalyst is ramped from ambient (i.e., 18° C.) to 250° C. at a rate of 10° C. per minute and held for 5 minutes. After 5 minutes, the sample is placed under vacuum at 250° C. for 30 minutes. After 30 minutes of vacuum, the sample is cooled to 35° C. at 20° C. per minute and held for 5 minutes. The oxygen and hydrogen isotherm is collected in increments at 35° C. between 0.50 and 760 mm Hg. Extrapolation of the linear portion of this curve to zero pressure gives the total (i.e., combined) adsorption uptake.

In another embodiment, the dehydrogenation catalyst comprises a first component comprising at least one metal component selected from Group 1 and Group 2 of the Periodic Table of Elements, such that the first component may comprise any combination or mixture of metal components selected from Groups 1 and 2 of the Periodic Table of Elements. Typically, the first component is present in an amount of at least 0.1 wt %, at least 0.2 wt %, at least 0.3 wt %, at least 0.4 wt %, at least 0.5 wt %, at least 0.6 wt %, at least 0.7 wt %, at least 0.8 wt %, at least 0.9 wt %, and at least 1.0 wt %. In one embodiment, the first component comprises at least one metal component selected from Group 1 of the Periodic Table of Elements, such as potassium, cesium, and rubidium; preferably potassium and potassium compounds. In another embodiment, the first component comprises at least one metal component selected from Group 1 of the Periodic Table of Elements. In still another embodiment, the first component comprises at least one metal component selected from Group 2 of the Periodic Table of Elements such as beryllium, calcium, magnesium, strontium, barium, and radium; preferably calcium and magnesium. Typically, the first component is present in an amount between about 0.1 wt % and about 5 wt % of the catalyst or between about 0.2 wt % and about 4 wt % of the catalyst or between about 0.3 and about 3 wt % of the catalyst. In one embodiment, the first component is present in an amount of about 0.15 wt % to about 0.6 wt % of the catalyst.

In addition, such a dehydrogenation catalyst comprises a second component comprising at least one metal component selected from Groups 6 to 10 of the Periodic Table of Elements, such as platinum and palladium such that the second component may comprise any combination or mixture of metal components selected from Groups 6 to 10 of the Periodic Table of Elements. In another embodiment, the second component comprises at least one metal component selected from Group 10 of the Periodic Table of Elements. Typically, the second component is present in an amount between about 0.1 wt % and about 10 wt % of the catalyst.

The term "metal component" is used herein to include a metal compound that may not be purely the elemental metal, but could, for example, be at least partly in another form, such as an oxide, hydride or sulfide form. The weight % (wt %) of the metal component is herein defined as being measured as the metal present based on the total weight of the catalyst composition irrespective of the form in which the metal component is present.

Suitable conditions for the dehydrogenation step comprise a temperature of about 250° C. to about 500° C. and/or a pressure of about 0.01 atm to about 20 atm (1 kPa to 2000 kPa), such as a temperature of about 300° C. to about 450° C. and a pressure of about 1 atm to about 3 atm (100 kPa to 300 kPa). To improve catalyst stability and assist in extracting the hydrogen generated in the dehydrogenation reaction, hydrogen may be co-fed to the dehydrogenation reaction, typically such that the molar ratio of hydrogen to cyclohexanone in the dehydrogenation feed is about 0:1 to about 4:1.

The reactor configuration used for the dehydrogenation process generally comprises one or more fixed bed reactors containing the dehydrogenation catalyst. Provision can be made for the endothermic heat of reaction, preferably by multiple adiabatic beds with interstage heat exchangers. The temperature of the reaction stream drops across each catalyst bed, and then is raised by the heat exchangers. Preferably, 3 to 5 beds are used, with a temperature drop of about 30° C. to about 100° C. across each bed. Preferably, the last bed in the series runs at a higher exit temperature than the first bed in the series.

By employing the present dehydrogenation process, substantially all the cyclohexanone in the cyclohexylbenzene hydroperoxide cleavage effluent can be converted to phenol. In practice, however, depending on market conditions, there is likely to be a significant demand for cyclohexanone product. This can readily met using the present process by reliance on the reversible nature of the reaction (2), namely by hydrogenating at least some of the phenol back to cyclohexanone. This can readily be achieved by, for example, contacting the phenol with hydrogen in the presence of a hydrogenation catalyst, such as platinum or palladium, under conditions including a temperature of about 20° C. to about 250° C., a pressure of about 101 kPa to about 10000 kPa and a hydrogen to phenol molar ratio of about 1:1 to about 100:1.

Dehydrogenation Effluent

The effluent from the cyclohexanone dehydrogenation reaction (also referred to as the dehydrogenation effluent) is composed mainly of phenol and hydrogen. The desired phenol is easily removed from the dehydrogenation effluent by fractionation to leave a hydrogen stream which, after suitable purification, can be recycled to the benzene hydroalkylation step.

Examples of contaminants that may be present in the dehydrogenation effluent, and possible amounts thereof, include (weight-parts-per-million (wppm) and wt % are based upon total weight of the dehydrogenation effluent):

water, e.g., at least 100 wppm and no greater than 3.0 wt %;
olefins, such as pentene and hexene, in any isomer e.g., at least 10 wppm and no greater than 3.0 wt %, each or in total;
acyclic alkylcyclohexanes, also including olefins as alkyl groups, such as pentylcyclohexane as any isomer, e.g., at least 10 wppm and no greater than 3.0 wt %, each or in total;
cyclic and acyclic alkylbenzenes, also including olefins as alkyl groups, such as toluene, ethylbenzene, n-propylbenzene, n-butylbenzene, n-pentylbenzene, cyclopentylbenzene and pentenylbenzene as any isomer, e.g., at least 10 wppm and no greater than 3.0 wt %, each or in total;
twelve carbon, two ringed hydrocarbons, such as cyclohexylbenzene, bicyclohexane, cyclohexenylcyclohexane, and cyclohexadienylcyclohexane, cyclohexenylbenzene, cyclohexadienylbenzene, and biphenyl, e.g., at least 10 wppm and no greater than 3.0 wt %, each or in total;
saturated and unsaturated ketones in any isomer, such as pentanones, methylcyclopentanones, hexanones, methylcyclopentenone, cyclohexylidene cyclohexanone, and cyclohexenyl cyclohexanone, e.g., at least 10 wppm and no greater than 4.0 wt %, each or in total;
cyclohexyldione(s), e.g., at least 10 wppm and no greater than 1.0 wt % in total;
less than 12 carbon, unsaturated hydrocarbons, cyclic and acyclic, or combinations thereof, such as cyclohexene, e.g., at least 10 wppm and no greater than 1.0 wt %, each or in total;
cyclohexanol, e.g., at least 10 wppm and no greater than 15.0 wt %;
cyclohexenone(s), e.g., 2-cyclohexenone or 3-cyclohexenone, e.g., at least 10 wppm and no greater than 2.0 wt %, each or in total;
hydroxycyclohexanone(s), such as 2-hydroxycyclohexanone, e.g., at least 10 wppm and no greater than 2.0 wt % in total;
aldehydes, especially, pentanals, hexanals, cyclohexyl, or methylcyclopentyl alkyl aldehydes, such 5-cyclohexyl hexanal, and 6-hydroxy-5-cyclohexyl hexanal, e.g., at least 10 wppm and no greater than 1.0 wt %, each or in total;
cyclohexyl phenol(s) and cyclohexenyl phenol(s), in any isomer e.g., at least about 10 wppm and no greater than 5.0 wt %, each or in total;
phenyl phenol(s), in any isomer e.g., at least about 10 wppm and no greater than 5.0 wt %, each or in total; and/or
dicyclic ethers and furans, such as dicyclohexylether, phenylcyclohexylether, diphenylether and dibenzofuran, e.g., at least 10 wppm and no greater than 1.5 wt %, each or in total.

Contaminant Treatment

In various embodiments, the cleavage effluent and/or the dehydrogenation effluent may comprise one or more contaminants. In various embodiments disclosed herein, the processes disclosed herein further comprise contacting at least a portion of the contaminant with an acidic material to convert at least a portion of the contaminant to a converted contaminant.

Suitable acidic material for use in treating the cleavage effluent include microporous acidic materials, such as zeolites, aluminas and aluminosilicates, especially zeolites having a pore diameter over 4 Angstrom; cation exchange resins, especially sulfonic resins, such as Rohm & Haas Amberlyst 16; Bronsted acids, such as formic acid, acetic acid, hydrochloric acid, and sulfuric acid; sulfurous acid or salts thereof, such as sodium sulfate, sodium hydrogen bisulfite, and sodium metabisulfite; and aqueous acid solutions. In one embodiment, the acidic material used to treat the cleavage effluent comprises at least part of the acid catalyst used to promote the cleavage reaction.

Conveniently, the acidic material has a relatively low volatility, with a normal boiling point above phenol and/or cyclohexylbenzene, such that it will tend to distill in the bottoms product in subsequent fractionation operations that may be conducted.

The contaminant treatment can be conducted directly on the cleavage effluent and/or dehydrogenation effluent, or after one or more separations of the cleavage effluent and/or dehydrogenation effluent. For example, the cleavage effluent and/or dehydrogenation effluent may be separated (e.g., by distillation) into phenol-rich and cyclohexanone-rich fractions before or after the contaminants are subjected to contaminant treatment.

Suitable contaminant treatment conditions vary with the acidic material employed. Contaminant treatment conditions include a temperature of at least about 30° C., or at least about 35° C., or at least about 40° C., or at least about 50° C., or at least about 60° C., or at least about 70° C., or at least about 80° C., or at least about 90° C., or at least about 100° C. In various embodiments, the temperature is less than about 250° C., or less than about 225° C., or less than about 190° C., or less than about 180° C., or less than about 170° C., or less than about 160° C., or less than about 150° C., or less than about 140° C. The temperature may be any range of the aforementioned temperatures.

The pressure may be about 0.75 psig to about 500 psig (5 kPa to 3450 kPa), or about 10 psig to 200 psig (70 kPa to 1380 kPa) such that the cleavage effluent and/or dehydrogenation effluent is completely or predominantly in the liquid phase during the treatment.

In various embodiments, the pressure may be about 10 psig to about 200 psig (170 kPa to 1380 kPa) and the temperature may be about 60° C. to about 160° C., such that most of the cleavage effluent and/or dehydrogenation effluent is in the liquid phase.

In embodiments in which the acidic material is a solid microporous material (e.g., zeolites, aluminas, etc.), the pressure may be about 10 psig to about 200 psig (70 kPa to 1380 kPa) and the temperature may be about 100° C. to about 250° C., such that most of the cleavage effluent and/or dehydrogenation effluent is in the liquid phase.

In various embodiments in which the acidic material is a cation exchange resin, the pressure may be about 10 psig to about 200 psig (70 kPa to 1380 kPa) and the temperature may be about 30° C. to about 100° C., such that most of the cleavage effluent and/or dehydrogenation effluent is in the liquid phase.

It will be understood that the contaminants in all or a portion of the cleavage effluent and/or dehydrogenation effluent may be contacted with an acidic material, as disclosed herein. For example, contaminants in a distilled fraction of the entire cleavage effluent and/or dehydrogenation effluent containing an enriched or depleted concentration of phenol and/or cyclohexanone relative to the cleavage effluent and/or dehydrogenation effluent may be contacted with an acidic material as described herein. When a stream is described as being "enriched" or "rich in" in a specified species, it is meant that the wt % of the specified species in that stream is enriched relative to the feed stream prior to separation. For example, a "phenol-rich stream" is a stream in which the wt % of phenol in increased relative to the feed stream prior to separation. When a stream is described as being "depleted" in a specified species, it is meant that the wt % of the specified species in that stream is reduced relative to the feed stream prior to separation.

Additionally or alternatively, a filtered fraction of the entire cleavage effluent and/or dehydrogenation effluent with reduced amounts of filterable components may be contacted with an acidic material as described herein.

Additionally or alternatively, a fraction of the cleavage effluent and/or dehydrogenation effluent has undergone an absorbtion operation, such as a water wash, such that absorbable components are reduced in concentration prior to contact with an acidic material.

Additionally or alternatively, a fraction of the cleavage effluent and/or dehydrogenation effluent has undergone an adsorption operation, such as passing over a molecular sieve to remove water (e.g., a 3 A molecular sieve) with one or more adsorbable components are reduced in concentration prior to contact with an acidic material.

The contaminant reactor may be any vessel that allows contacting of the contaminant with an acidic material for a suitable residence time. For example, a contaminant reactor may be an open or substantially open vessel reactor or pipe.

In various embodiments, contaminants in more than one portion of the cleavage effluent and/or dehydrogenation effluent may be contacted with an acidic material. For example, the cleavage effluent and/or dehydrogenation effluent may be separated into one or more streams rich in cyclohexanone, phenol, and/or cyclohexylbenzene, relative to the cleavage effluent and/or dehydrogenation effluent and each stream may be contacted with an acidic material. The acidic material may be the same or different for each fraction.

In various embodiments, a given fraction of the cleavage effluent and/or dehydrogenation effluent may undergo more than one contacting steps with an acidic material. For example, a cyclohexanone-rich fraction derived from distillation of the entire cleavage effluent and/or dehydrogenation effluent may first be contacted with a first acidic material (e.g., sulfuric acid) and then separately exposed to a second acidic material (e.g., a cation exchange resin).

Non-limiting examples to the reactions that can occur in converting the contaminants in the cleavage effluent and/or dehydrogenation effluent to converted contaminants include:
  aldol condensation, especially of ketones and aldehydes;
  dehydration, especially of alcohols;
  alkylation, especially of olefins and alcohols with phenols or alkylatable aromatics.
  oligomerization of olefins;
  combinations of alkylation and cyclization of the alkylation products;
  esterification, especially of carboxylic acids and alcohols;
  cracking, especially of alkyl and aryl moieties;
  where the contaminant byproduct reacts with a phenol molecule;
  where the contaminant byproduct reacts with a cyclohexanone molecule;
  where the contaminant byproduct reacts with another contaminant byproduct of the same or different species; and
  any combination of the above.

In various embodiments, the converted contaminants include:
  a property that makes them more separable from phenol and/or cyclohexanone than the starting contaminant. "Separable" can mean distillable, e.g., the converted contaminant does not form an azeotrope with phenol and/or cyclohexanone, whereas the starting contaminant byproduct does; or filterable, or absorbable (e.g., in water or the aqueous acidic material), or adsorbable;
  a molecular weight higher than the starting contaminant;
  a molecular weight lower than the starting contaminant;
  a volatility lower than the starting contaminant, and conveniently considerably lower than cyclohexanone and/or phenol;

a volatility higher than the starting contaminant, conveniently considerably higher than cyclohexanone and/or phenol;

aldol condensation products, generally aldehydes and ketones;

water, generally from neutralization of bases;

alcohols, from saponification of esters; and acid salts, from a neutralization or saponification reaction.

In various embodiments, at least about 20.0%, or at least about 50.0%, or at least about 80.0%, or at least about 90.0%, or at least about 99.9%, or essentially all of any one contaminant is converted to a converted contaminant, based on weight %.

In various embodiments, at least about 20.0 wt %, or at least about 50.0 wt %, or at least about 80.0 wt %, or at least about 90.0 wt %, or at least about 99.9 wt % of any olefin contaminants, including furans and alcohols, are converted to a converted contaminant, the wt % based upon total weight of the stream.

In various embodiments, at least about 20.0 wt %, or at least about 50.0 wt %, or at least about 80.0 wt %, or at least about 90.0 wt %, or at least about 99.9 wt %, or essentially all of the contaminants present in the stream are converted to a converted contaminant, the wt % based upon total weight of the stream.

In various embodiments, a process for making phenol comprises: (a) contacting benzene and hydrogen with a hydroalkylation catalyst under hydroalkylation conditions to produce cyclohexylbenzene; (b) contacting at least a portion of the cyclohexylbenzene with an oxidation catalyst under oxidation conditions to produce cyclohexylbenzene hydroperoxide; (c) contacting at least a portion of the cyclohexylbenzene hydroperoxide with a cleavage catalyst under cleavage conditions to produce a cleavage effluent comprising phenol and cyclohexanone; (d) contacting at least a portion of the cyclohexanone from the cleavage effluent with a dehydrogenation catalyst under dehydrogenation conditions to produce a dehydrogenation effluent having at least a portion of the cyclohexanone converted to phenol, wherein the dehydrogenation effluent further comprises a first contaminant; and (e) contacting at least a portion of the first contaminant from the dehydrogenation effluent with an acidic material under contaminant treatment conditions to convert at least a portion of the first contaminant into a converted first contaminant.

In various embodiments, the first contaminant is produced in one or more of the contacting steps (a) to (d) described above. For example, first contaminant may be one or more of bicyclohexane, cyclohexylbenzene, methylcyclopentylbenzene, n-butylbenzene, n-pentylbenzene, pentenylbenzene, 2-hydroxycyclohexanone, cyclohexenone, cyclohexanol, cyclohexanone, cyclohexanedione, benzoic acid, hexanal, methycyclopentanone, hexanone, cyclohexenol and methylcyclopentenone.

In various embodiments, the process further includes contacting (i) at least a portion of the phenol from the cleavage effluent; and (ii) a second contaminant with the acidic material to convert at least a portion of the second contaminant to a converted second contaminant. In various embodiments, the second contaminant is produced in one or more of the contacting steps (a) to (c). For example, the second contaminant may be one or more of bicyclohexane, cyclohexylbenzene, methylcyclopentylbenzene, 2-hydroxycyclohexanone, cyclohexenone, cyclohexanol, cyclohexanone, cyclohexanedione, benzoic acid, hexanal, and methycyclopentanone.

In one embodiment, at least a portion of cleavage effluent and at least a portion of dehydrogenation effluent are combined and contacted with the acidic material.

In various embodiments, a process for making phenol comprises: (a) contacting benzene and hydrogen with a hydroalkylation catalyst under hydroalkylation conditions to produce cyclohexylbenzene; (b) contacting at least a portion of the cyclohexylbenzene with an oxidation catalyst under oxidation conditions to produce cyclohexylbenzene hydroperoxide; (c) contacting at least a portion of the cyclohexylbenzene hydroperoxide with a cleavage catalyst under cleavage conditions to produce a first effluent comprising phenol and cyclohexanone; (d) separating the first effluent into a first phenol-rich stream and a cyclohexanone-rich stream; (e) contacting at least a portion of the cyclohexanone-rich stream with a dehydrogenation catalyst under dehydrogenation conditions effective to form a second effluent having at least a portion of the cyclohexanone converted to phenol, wherein each of the first phenol-rich stream and the second effluent comprises a contaminant; (f) contacting at least a portion of the second effluent and optionally the first phenol-rich stream with an acidic material to form a third effluent having at least a portion of the contaminant converted into a converted contaminant; and (g) separating the third effluent into a second phenol-rich stream and a converted contaminant-rich stream.

Processing of Contaminant-Treated Stream

In various embodiments, after one or more contaminants in the cleavage effluent and/or dehydrogenation effluent is contacted with an acidic material to form contaminant-treated stream, it may be separated into one or more streams rich in phenol, cyclohexanone and/or cyclohexylbenzene, relative to the feed stream. These streams may be substantially or completely free of contaminants.

In various exemplary embodiments, the process further comprises separating the contaminant-treated stream into a first stream that is enriched in cyclohexanone or phenol or both and a second stream that is enriched in converted contaminant relative to the contaminant-treated stream.

Heat Treatment

In various embodiments, some or all of the contaminants (e.g., in the cleavage effluent and/or dehydrogenation effluent or some portion of the cleavage effluent and/or dehydrogenation effluent) are subjected to heat treatment conditions upstream or downstream of the contaminant treatment step.

For example, the temperature of all or a portion of the cleavage effluent and/or dehydrogenation effluent may be raised to at least about 100° C., or about 150° C. to about 185° C., or at least about 200° C. to produce a heat-treated cleavage effluent and/or dehydrogenation effluent. In various embodiments, the temperature may be less than about 250° C., or less than about 225° C. The temperature may be any range of the aforementioned temperatures. In various embodiments, the heat treatment conditions include a residence time may be at least 1 min., 2 min., 3 min., 5 min., 10 min., or 15 min. The residence time may be less than about 120 min., 60 min., or 30 min. The residence time may be any logical range of the aforementioned times.

In one embodiment, during heat treatment at least about 1 wt %, or 10.0 wt %, or 20.0 wt %, or 50.0 wt %, or 80.0 wt %, or 90.0 wt %, or 99.0 wt %, or 99.9 wt %, or all of any one contaminant (e.g., hydroxycyclohexanone, or other oxyketones, such as hexanophenone, 6-hydroxyhexanophenone, 6-hydroperoxyhexanophenone, benzoic acid, pentanal, pentanone, 2-hydroxycyclohexanone, phenylcyclohexanone, or unreacted peroxides) is converted to a converted contaminant.

In various embodiments, no greater than about 80.0 wt %, or 50.0 wt %, or 30.0 wt %, or 20.0 wt %, or 10.0 wt % of contaminant hydroxycyclohexanone or other oxyketones such as 6-hydroxyhexanophenone, or both are converted to a converted contaminant including a furan with both an olefin and oxygen moiety, such as 1,2,4a,9b-tetrahydrodibenzo[b,d]furan, that may result from the dehydration, alkylation, and cyclization reaction of phenol and hydroxycyclohexanone.

In various embodiments, the heat-treated stream may be separated into one or more streams rich in one or more of cyclohexanone, phenol, and/or cyclohexylbenzene, relative to the heat-treated stream. These fractions may comprise little or no converted contaminants.

The heat treatment may be conducted in a simple vessel or pipe, which may be open or have means for mixing, such as baffles or a static mixer for turbulent flow. Further, the heat treatment may take place in a fractionation column, wherein fractionation operating conditions are selected such that the components distilled are exposed to the temperatures and residence times noted at any point or points in the column. The heat treated components may be withdrawn from any point in the fractionation column, as an overhead, bottom or side composition product. Generally, the heat treatment converts at least some of the contaminants or converted contaminants to other compounds more readily removed from the phenol and/or cyclohexanone.

After contaminant treatment and/or heat treatment or combined contaminant and heat treatment, the converted contaminants will generally have a property that makes them more separable from phenol or cyclohexanone, or both, than the starting contaminant. Separable can be distillable, e.g., the converted contaminant does not form an azeotrope with phenol or cyclohexanone whereas the starting contaminant does, and/or filterable, and/or absorbable. As a result, following contaminant and/or heat treatment, the stream can be subjected to one or more separations ultimately resulting in streams that predominantly comprise cyclohexanone, phenol, and converted contaminant.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam, and nylons, such as nylon 6 and nylon 6,6.

The phenol produced through the processes disclosed herein may be used, for example, to produce phenolic resins, bisphenol A, ε-caprolactam, adipic acid, and/or plasticizers.

Phenol Compositions

In various embodiments, the methods of the invention described herein create compositions that are rich in phenol (also referred to as phenol compositions).

Conveniently, the compositions rich in phenol comprise at least 95 wt % phenol, or at least 98 wt % phenol, or at least 99 wt % phenol, or at least 99.5 wt % phenol, or at least 99.9 wt % phenol, or at least 99.99 wt % phenol, based upon total weight of the composition.

In various embodiments, the compositions rich in phenol further comprise at least one of the following components: bicyclohexane, cyclohexylbenzene, methylcyclopentylbenzene, n-butylbenzene, n-pentylbenzene, pentenylbenzene, hydroxycyclohexanone, cyclohexenone, cyclohexanol, cyclohexanone, cyclohexanedione, benzoic acid, hexanal, methycyclopentanone, hexanone, cyclohexenol, and methylcyclopentenone. As used herein, these components are collectively referred to as the "Seventeen Components."

Conveniently, the lower limit of the concentration of one or more of the Seventeen Components in the composition rich in phenol may be 0.1 wppm, or 0.5 wppm, or 1 wppm, or 2 wppm or 5 wppm, based upon the total weight of the composition. The upper limit of the concentration of one or more of the Seventeen Components in the composition rich in phenol may be 1000 wppm, or 100 wppm, or 10 wppm, or 3 wppm or 1 wppm, based upon the total weight of the composition. The concentration of one or more of the Seventeen Components in the composition may be any combination of the upper and lower limits described above.

The compositions rich in phenol may comprise the above-described concentrations of any number of the Seventeen Components in any combination. For example, the phenol composition may comprise at least 99.900 wt % phenol and at least 0.1 wppm and no greater than 1000 wppm of pentylbenzene, and no other component in the group. As another example, the phenol composition may comprise at least 99.900 wt % phenol, at least 0.1 wppm and no greater than 1000 wppm of bicyclohexane, at least 0.1 wppm and no greater than 1000 wppm of cyclohexylbenzene, and at least 0.1 wppm and no greater than 1000 wppm of cyclohexenol, and no other component in the group. As another example, the phenol composition may comprise at least 99.900 wt % phenol, and at least 0.1 wppm and no greater than 1000 wppm of each one of the Seventeen Components. This illustration similarly applies to phenol compositions having other upper and lower limits of the concentrations of the Seventeen Components.

In various embodiment, the composition comprises:
(a) at least 99 wt % phenol; and
(b) 0.1 wppm to 1000 wppm of at least one of the following components: bicyclohexane, cyclohexylbenzene, methylcyclopentylbenzene, n-butylbenzene, n-pentylbenzene, pentenylbenzene, hydroxycyclohexanone, cyclohexenone, cyclohexanol, cyclohexanone, cyclohexanedione, benzoic acid, hexanal, methycyclopentanone, hexanone, cyclohexenol and methylcyclopentenone, wherein the wt % and wppm are based upon the total weight of the composition.

In various embodiments, the combined amount of the Seventeen Components present in the composition accounts for at least 5 wt %, or at least 10 wt %, or at least 20 wt %, or at least 30 wt %, or at least 40 wt %, or at least 50 wt % of the total amount of contaminants in the composition. As used herein, "the total amount of contaminants in the composition" means all species present in the composition by weight excluding phenol.

In various embodiments, the total combined amount of the Seventeen Components present in the phenol composition does not exceed 1000 wppm, or does not exceed 100 wppm, or does not exceed 50 wppm, or does not exceed 25 wppm, or does not exceed 10 wppm, or does not exceed 3 wppm, or does not exceed 1 wppm.

The concentration ranges of components in the compositions described herein may be measured according to the gas chromatograph (GC) technique described in ASTM D 6142-08, tailored, and calibrated for such components.

In various embodiments, one or more of the Seventeen Components present in the composition were generated in situ during a process for making phenol (i.e., were not added from an external source).

In various embodiments, one or more of the Seventeen Components were produced during at least one of the steps of:
(i) hydroalkylating benzene to produce cyclohexylbenzene;

(ii) oxidizing cyclohexylbenzene to produce cyclohexylbenzene hydroperoxide;
(iii) cleaving cyclohexylbenzene hydroperoxide to form phenol and cyclohexanone; and
(iv) dehydrogenating at least some cyclohexanone into phenol.

In various embodiments, the concentration of oxygenate components that are likely to cause problems in further processing are relatively low compared to the concentration of hydrocarbon components which are relatively benign in further processing.

In one embodiment, a novel phenol composition may comprise:
(a) at least 99.900 wt % phenol;
(b) at least 0.1 wppm and no greater than 10 wppm of at least one of the following components: bicyclohexane, cyclohexylbenzene, methylcyclopentylbenzene, n-butylbenzene, n-pentylbenzene, and pentenylbenzene; and
(c) at least 0.1 wppm and no greater than 3 wppm of one or more of the following oxygenate components: hydroxycyclohexanone, cyclohexenone, cyclohexanol, cyclohexanone, cyclohexanedione, benzoic acid, hexanal, methycyclopentanone, hexanone, cyclohexenol, and methylcyclopentenone.

In another embodiment, the phenol composition may comprise at least 99.900 wt % phenol, and at least 0.1 wppm to no greater than 3 wppm of one or more hydrocarbon components and at least 0.1 wppm to no greater than 1 wppm of one or more oxygenate components.

Any of the phenol compositions discussed herein may additionally comprise at least 0.1 wppm to 1000 wppm water, or at least 0.1 wppm to 150 wppm water. ASTM D 1631 may be used to measure water content.

Also, any of the phenol compositions discussed herein may further contain less than 100 wppm, or less than 10 wppm, or less than 1 wppm, or no measurable concentration of at least one or any combination of hydroxyacetone, mesityl oxide, 2-methylbenzofuran, acetophenone, alpha-methylstyrene, cumene, 2-phenylpropanal, tert-butylbenzene and sec-butylbenzene. These components, typically produced by conventional methods, are particularly problematic in further processing of a phenol composition, and are virtually non-existent in the method of the present invention. As used herein, "no measurable concentration" means the quantity of these components in the composition is below the detectable limit in the gas chromatographic measurement technique described in ASTM D 6142-08 specifically tailored and calibrated for these components.

Finally, any of the phenol compositions discussed herein may have acceptable or exceptional quality according to any industry standard specifications. These specifications may include, for example, density of 1.047-1.053 g/ml (for example, as determined by ASTM D 3505); freezing point of at least 40.6° C., such as 40.9° C. (for example, as determined by ASTM D1493); color in the molten state of 20 maximum, or 10 maximum, or 5 maximum, as determined by ASTM D1686-10 Standard Test Method for Color of Solid Aromatic Hydrocarbons and Related Materials in the Molten State (Platinum-Cobalt Scale); Sulfuric Acid Discoloration (SAD) of 95% transmission or better (determined according to the color test procedure described in U.S. Pat. No. 4,480,134 Col. 5 lns 49-61); total organic impurities of no greater than 4000 wppm, such as no greater than 30 wppm (for example, as determined by ASTM D6142-08); and a cresol content of no greater than 10 wppm (for example, as determined by ASTM D6142-08).

The invention will now be more particularly described with reference to the following non-limiting Examples and the accompanying drawings.

Example 1 (Comparative)

Production of Catalyst Comprising 1% Pt, 0.50% K on a Silica Support

A 1/20 inch (0.13 cm) silica extrudate was impregnated with 0.50 wt % K as potassium carbonate using incipient wetness impregnation and dried at 121° C. After drying the 0.50 wt % potassium containing silica extrudate was calcined in air at 538° C. The calcined 0.50% K containing silica extrudate was then impregnated with 1% Pt as tetraammine platinum hydroxide using incipient wetness impregnation and dried at 121° C. After drying the 1% Pt, 0.50% K containing silica extrudate was calcined in air at 350° C.

Example 2

Production of 0.1% Sn/1% Pt/$SiO_2$ Catalyst

A catalyst was prepared by initially impregnating a silica extrudate with an aqueous solution of tetraammine Pt nitrate. After drying in air at 121° C., the resultant platinum-containing extrudate was impregnated with an aqueous solution of tin chloride and then dried in air at 121° C. Part of the resultant product was retained (uncalcined catalyst 2A) and part was calcined in air at 350° C. for 3 hours before being used in subsequent catalyst testing (calcined catalyst 2B). The compositions of the catalysts are summarized in Table 1.

Examples 3 to 8

Production of 1% Pt/x % Sn/$SiO_2$ Catalyst

Five additional catalysts containing 1 wt % platinum and varying amounts of tin, namely 0.05 wt % (Example 3), 0.1 wt % (Example 4), 0.15 wt % (Example 5), 0.25 wt % (Example 6), 0.5 wt % (Example 7), and 1 wt % (Example 8), were prepared by incipient wetness impregnation. In each case, a 1/20 inch quadrulobe silica extrudate was initially impregnated with an aqueous solution of tin chloride and then dried in air at 121° C. The resultant tin-containing extrudates were then impregnated with an aqueous solution of tetra amine Pt nitrate and again dried in air at 121° C. Each of resultant products was calcined in air at 350° C. for 3 hours before being used in subsequent catalyst testing. The compositions of the catalysts are summarized in Table 1.

Example 9

Production of 1% Pt/1% Sn/0.5% K/$SiO_2$ Catalyst

A potassium, tin and platinum containing 1/20" quadrulobe silica extrudates was prepared by incipient wetness impregnation. Initially, the silica extrudate was impregnated with an aqueous solution of potassium carbonate, then dried in air at 121° C. and calcined again in air at 538° C. for 3 hours. The potassium-containing extrudate was then impregnated with an aqueous solution of tin chloride and then dried in air at 121° C. The resultant potassium and tin-containing extrudate was then impregnated with an aqueous solution of tetraammine Pt nitrate and again dried in air at 121° C. Each of resultant products was divided into two parts; a first part, designated A, which was used without calcination in subsequent catalyst testing and a second part, designated B, which was calcined in air at 350° C. for 3 hours before being used in subsequent catalyst testing. The compositions of the catalysts are summarized in Table 1.

Example 10

Chemisorption Testing

The hydrogen and oxygen chemisorption of each of the calcined and uncalcined samples of Examples 1 to 9 was measured on a Micromeritics ASAP2010 instrument using the following chemisorpton procedure.

| Task | Step | Gas | Temp (° C.) | Rate (° C./min) | Time (min) |
|---|---|---|---|---|---|
| 1 | Flow | Helium | 200 | 10 | 30 |
| 2 | Flow | Hydrogen | 250 | 10 | 30 |
| 3 | Flow | Helium | 250 | 10 | 5 |
| 4 | Evacuation | | 250 | 0 | 60 |
| 5 | Evacuation | | 35 | 20 | 5 |
| 6 | Leak Test | | 35 | 0 | |
| 7 | Isotherm | Hydrogen or Oxygen | 35 | 0 | |

The chemisorption results are summarized in Table 1.

Example 11

Benzene Hydrogenation Testing

Certain of the catalysts of Examples 1 to 9 were further characterized by measuring their benzene hydrogenation activity ($1^{st}$ order rate constant at 100° C.) using the following procedure.
1. Purge—Start helium flow at 200 sccm, purge time 5 mins
2. Drying—Ramp to 110° C. at 5° C./min, hold time for 60 mins
3. Reduction—reduce at 350° C. (for Pd) 250° C. (for Pt), $H_2$ flow at 200 sccm, hold time of 1 hr.
4. Reaction temperature range is 50° C., 75° C., 100° C., 125° C., $1^{st}$ order rate constant at 100° C. is reported as the BHA No. in Table 1.

TABLE 1

| Example | Pt, wt % | Sn, wt % | K, wt % | $H_2$ Dispersion | $O_2$ Dispersion | BHA |
|---|---|---|---|---|---|---|
| 2A | 1 | 0.10 | 0 | 24% | 26% | 330 |
| 2B | 1 | 0.10 | 0 | 35% | 29% | 170 |
| 3 | 1 | 0.05 | 0 | 54% | 36% | 200 |
| 4 | 1 | 0.10 | 0 | 34% | 25% | 150 |
| 5 | 1 | 0.15 | 0 | 9% | 29% | 85 |
| 6 | 1 | 0.25 | 0 | 5% | 21% | 21 |
| 7 | 1 | 0.5 | 0 | 4% | 20% | 16 |
| 8 | 1 | 1 | 0 | 1% | 16% | 2 |
| 9A | 1 | 1 | 0.5 | 1% | 16% | 21 |
| 9B | 1 | 1 | 0.5 | 1% | 6% | 2 |

Example 12

Cyclohexanone (CHO) Dehydrogenation Testing

The reactor used in these experiments consisted of a 316 stainless steel tube with dimensions of 22 inches (56 cm) long, 0.5 inch (1.3 cm) outside diameter and 0.035 inch (0.09 cm) wall thickness. A piece of 316 stainless steel tubing 8.75 inches (22 cm) long and 0.375 inch (0.95 cm) outside diameter and a piece of 0.25 inch (0.64 cm) tubing of similar length was used in the bottom of the reactor as a spacer (one inside of the other) to position and support the catalyst in a isothermal zone of a furnace. A 0.25 inch (0.64 cm) plug of glass wool was placed at the top of the spacer to keep the catalyst in place. A 0.125 inch (0.32 cm) stainless steel thermo-well was placed in the catalyst bed, the thermo-well being long enough to monitor temperature throughout the catalyst bed using a movable thermocouple.

Each catalyst sample was pressed into pellets then crushed and sized to 20-40 US sieve mesh. Typically 5.0 grams, volume 12.5 cc, of the catalyst was presized to 20-40 mesh and used as a standard loading. The catalyst was then loaded into the reactor from the top. The catalyst bed typically was 15 cm in length. A 0.25 inch (0.64 cm) plug of glass wool was placed at the top of the catalyst bed to separate quartz chips from the catalyst. The remaining void space at the top of the reactor was filled with quartz chips. The reactor was installed in the furnace with the catalyst bed in the middle of the furnace at a pre-marked isothermal zone. The reactor was then pressure and leak tested typically at 300 psig (2170 kPa).

Each catalyst sample was pre-conditioned in situ by heating to 375° C. to 460° C. with $H_2$ flow at 100 cc/min and held for 2 hours. A 500 cc ISCO syringe pump was used to introduce the cyclohexanone to the reactor. The feed was pumped through a vaporizer before flowing through heated lines to the reactor. A Brooks mass flow controller was used to set the hydrogen flow rate. A Grove "Mity Mite" back pressure controller was used to control the reactor pressure typically at 100 psig (790 kPa). GC analyses were taken to verify feed composition. The feed was then pumped through the catalyst bed held at the reaction temperature of 375° C. to 460° C., preferably at 460° C., at a WHSV of 2-15 and a pressure of 100 psig (790 kPa). The products exiting the reactor flowed through heated lines routed to two collection pots in series. The non-condensable gas products routed to an online HP 5890 GC. The first pot was heated to 60° C. and the second pot cooled with chilled coolant to about 10° C. Material balances were taken at 12 to 24 hrs intervals. Samples were taken and diluted with 50% ethanol for analysis. A Hewlett Packard 6890 gas chromatograph with FID detector and with an Agilent technologies GC column 30 m×0.32 mm×0.25 micron film thickness was used for the analyses of the hydrocarbon products. Non-condensable gas products analyses were taken online via a HP 5980 Gas Chromatograph with J and W Scientific column 60 m×0.25 mm ID×1.0 micron film. The HP 6890GC analysis ramp program was set to: 40° C. for 0 min; 5° C./min to 150° C., held 0 min; 10° C./min to 260° C. held 28 min; total analysis time was 60 min; and the HP 5890 GC ramp was set to: −30° C. for 5 min, 5° C./min to 80° C. for 2 min, 5° C./min to 200° C. for 0 min, 15° C./min to 240° C. held to the end, total analysis time of 60 min.

The results of the cyclohexanone testing of the catalysts of Examples 1 to 9 are summarized in the accompanying drawings.

Figure 2:
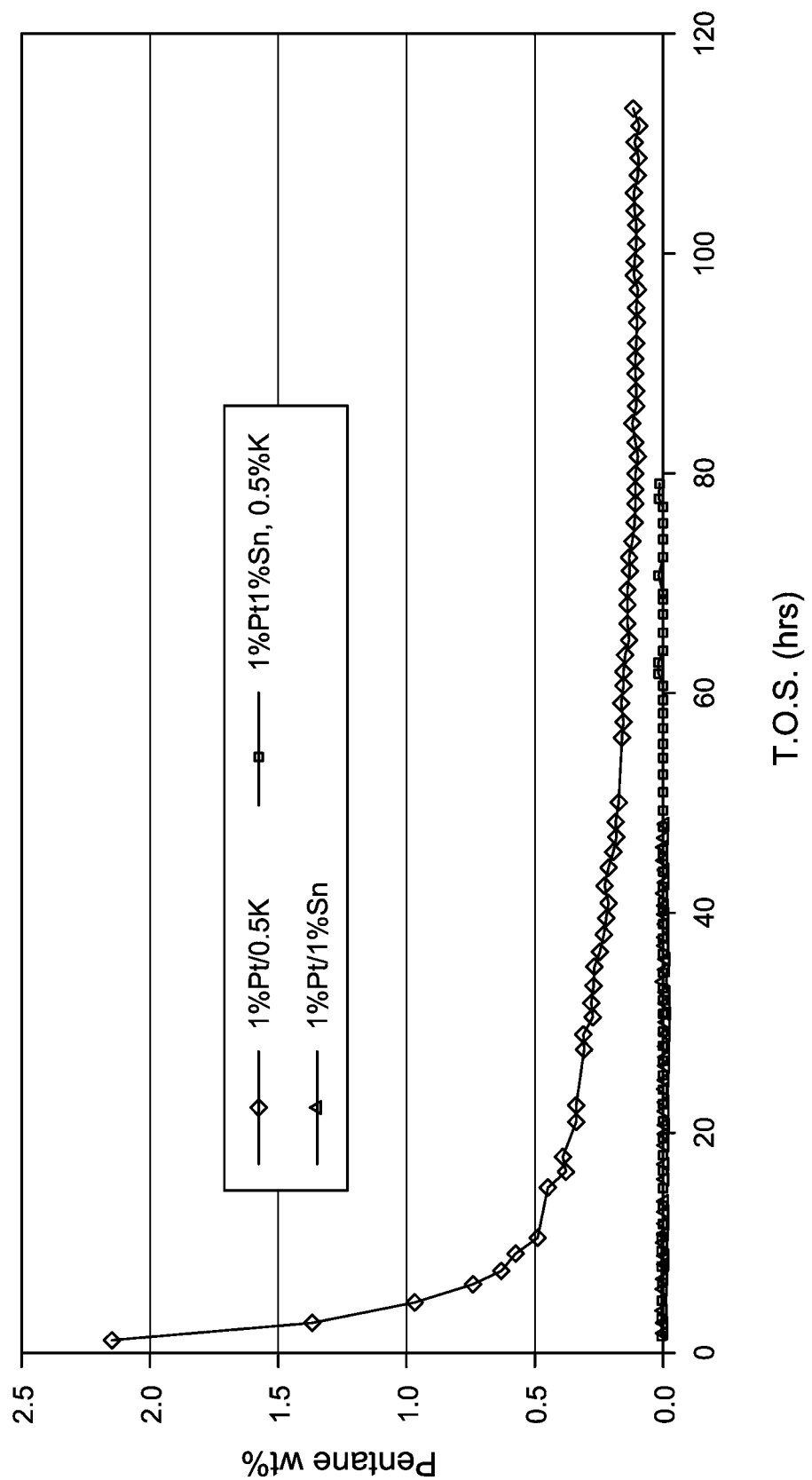
FIG. 2 is a graph comparing pentane production against time on stream for the 1% Pt/1% Sn/SiO$_2$ catalyst of Example 7 and the 1% Pt/1% Sn/0.5% K/SiO$_2$ catalyst of Example 9B with that of the 1% Pt/0.5% K/SiO$_2$ catalyst of Comparative Example 1.

FIG. 1 show that presence of Sn at 1 wt % in a calcined 1 wt % Pt/$SiO_2$ catalyst, both with and without the presence of 0.5 wt % K (Examples 9B and 8, respectively) resulted in lower catalyst activity and higher catalyst deactivation compared to the catalyst of Comparative Example 1 without Sn. This is illustrated with reference to conversion of cyclohexanone (CHO). However, a dramatic decrease in the pentane formation was observed (FIG. 2). When 0.10 wt % Sn was added to the Pt/support without and with calcination, Examples 2A and 2B, the data show that this approach improves the catalyst activity and higher cyclohexanone conversion was obtained.

Figure 3:
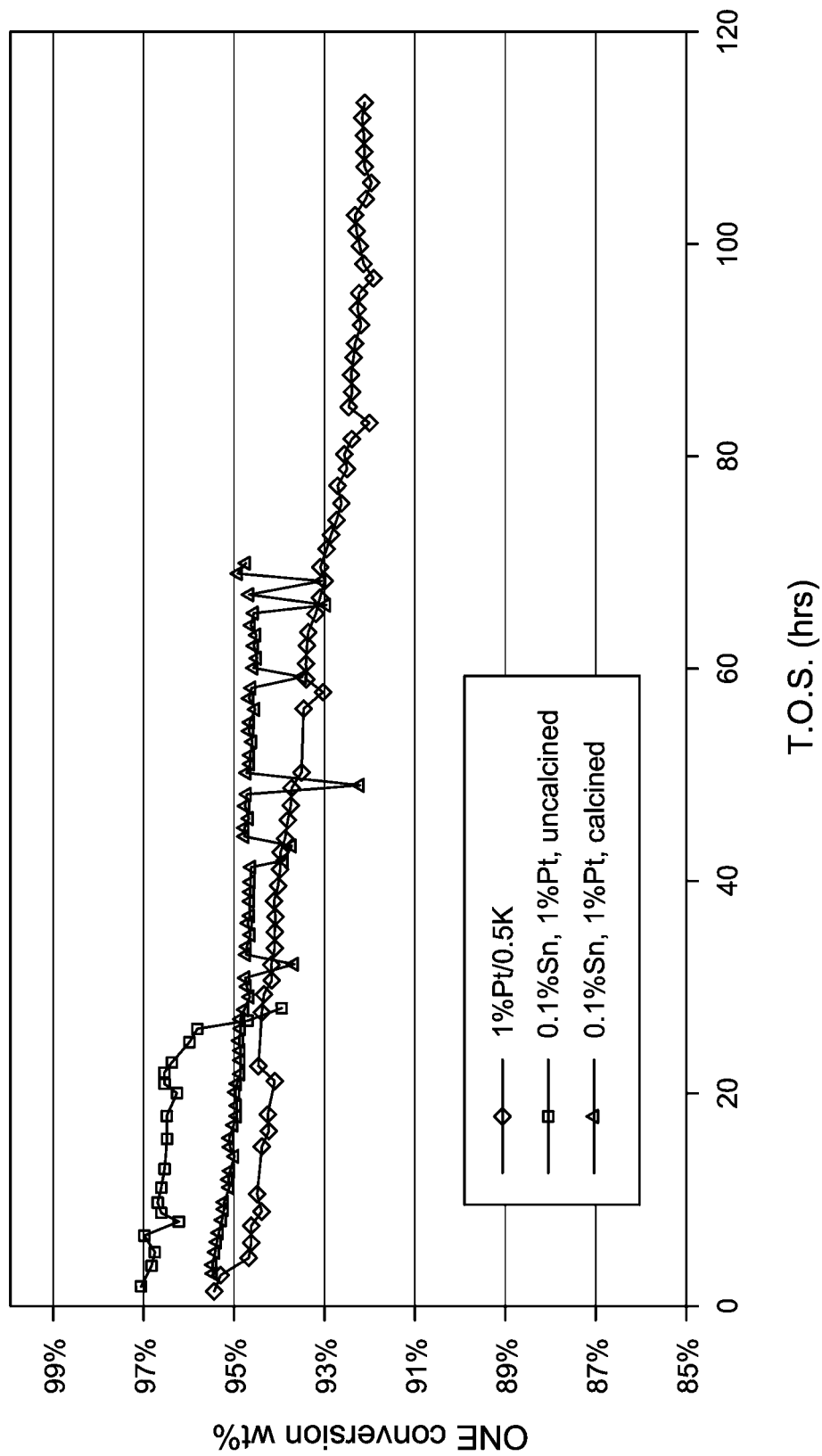
FIG. 3 is a graph comparing cyclohexanone conversion against time on stream for the uncalcined and calcined 0.1% Sn/1% Pt/SiO$_2$ catalysts of Examples 2A and 2B with that of the 1% Pt/0.5% K/SiO$_2$ catalyst of Comparative Example 1.
Figure 4:
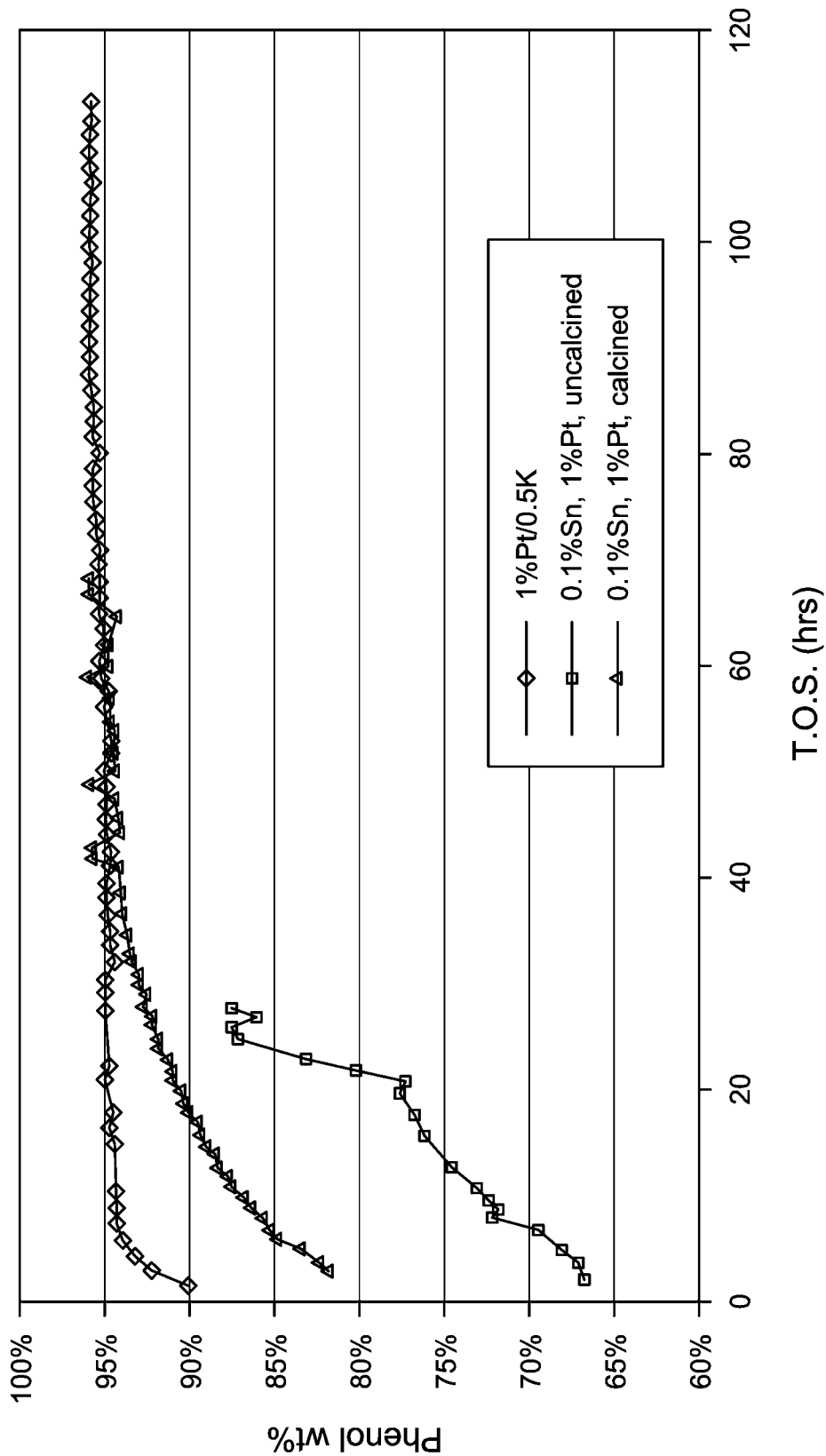
FIG. 4 is a graph comparing phenol production against time on stream for the uncalcined and calcined 0.1% Sn/1% Pt/SiO$_2$ catalysts of Examples 2A and 2B with that of the 1% Pt/0.5% K/SiO$_2$ catalyst of Comparative Example 1.
Figure 5:
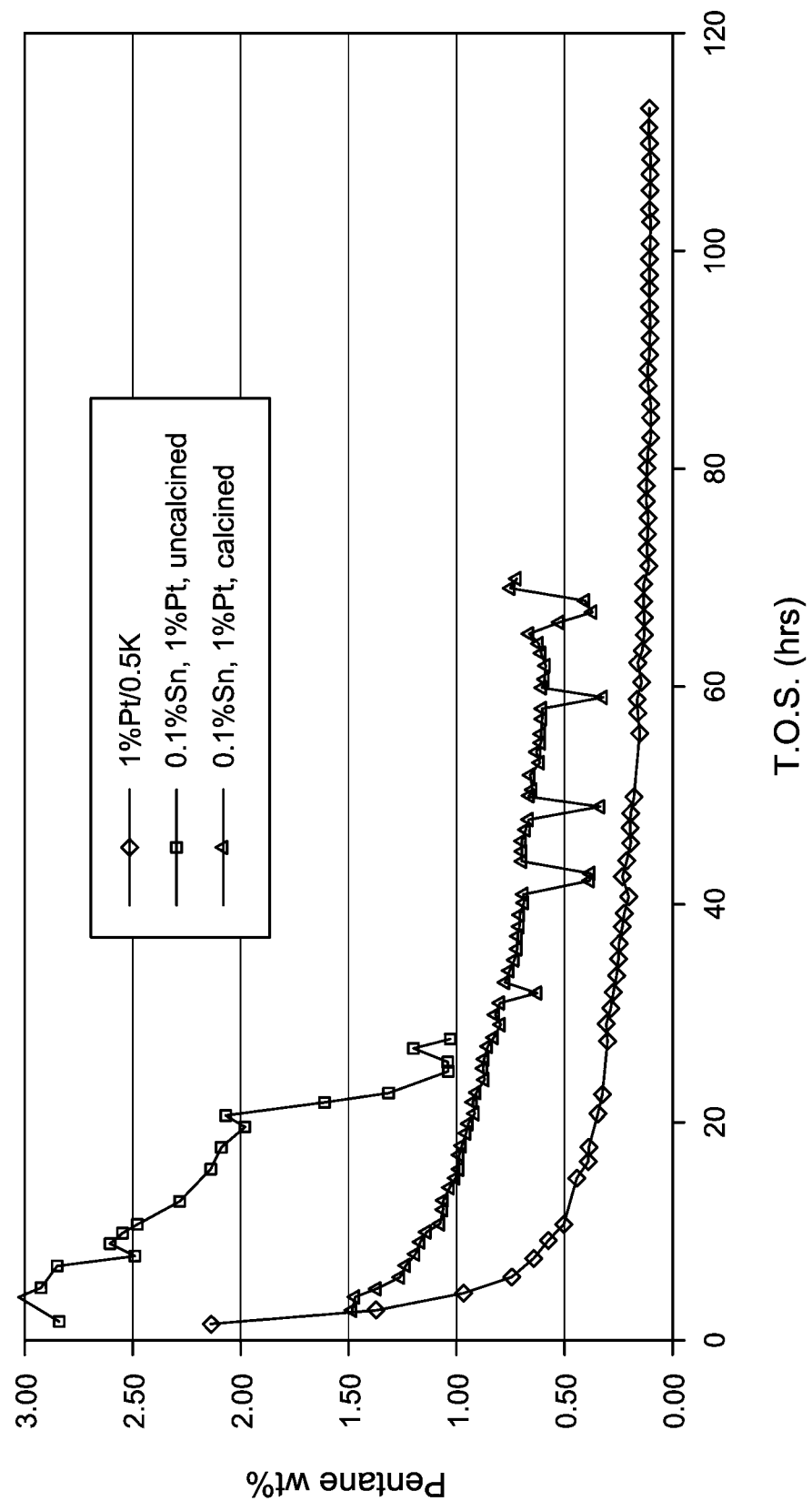
FIG. 5 is a graph comparing pentane production against time on stream for the uncalcined and calcined 0.1% Sn/1% Pt/SiO$_2$ catalysts of Examples 2A and 2B with that of the 1% Pt/0.5% K/SiO$_2$ catalyst of Comparative Example 1.

The calcined sample of Example 2B shows better stability than the non-calcined sample of Example 2A and the K/Pt catalyst of Comparative Example 1 (FIG. 3). The calcined sample of Example 2B also shows better selectivity to phenol than the non-calcined sample of Example 2A (FIG. 4), but its pentane selectivity is higher than the Pt/K catalyst of Comparative Example 1 (FIG. 5).

Figure 6:
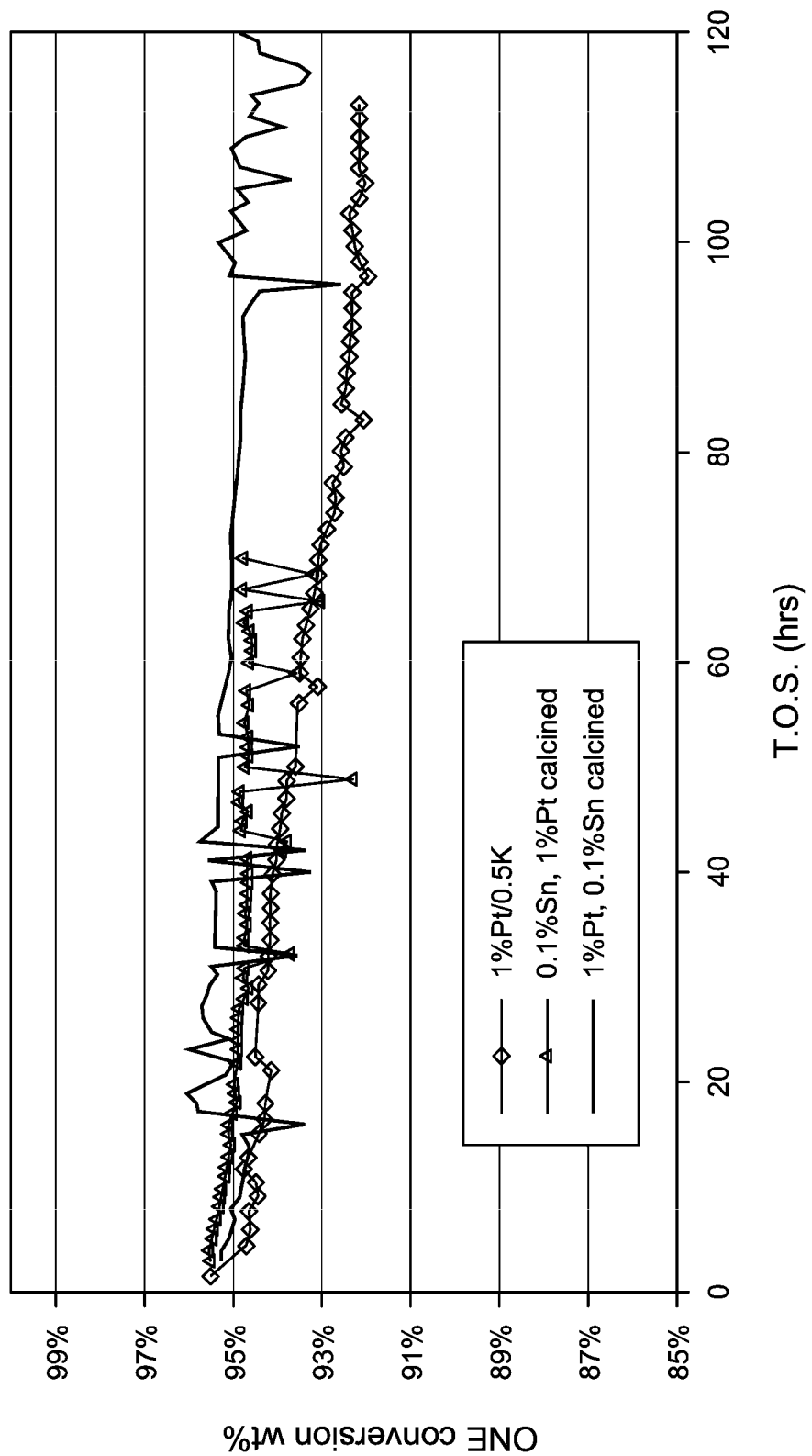
FIG. 6 is a graph comparing cyclohexanone conversion against time on stream for the calcined 1% Pt/0.1% Sn/SiO$_2$ catalyst of Example 4 with that of the calcined 0.1% Sn/1% Pt/SiO$_2$ catalyst of Example 2B and that of the calcined 1% Pt/0.5% K/SiO$_2$ catalyst of Comparative Example 1.
Figure 7:
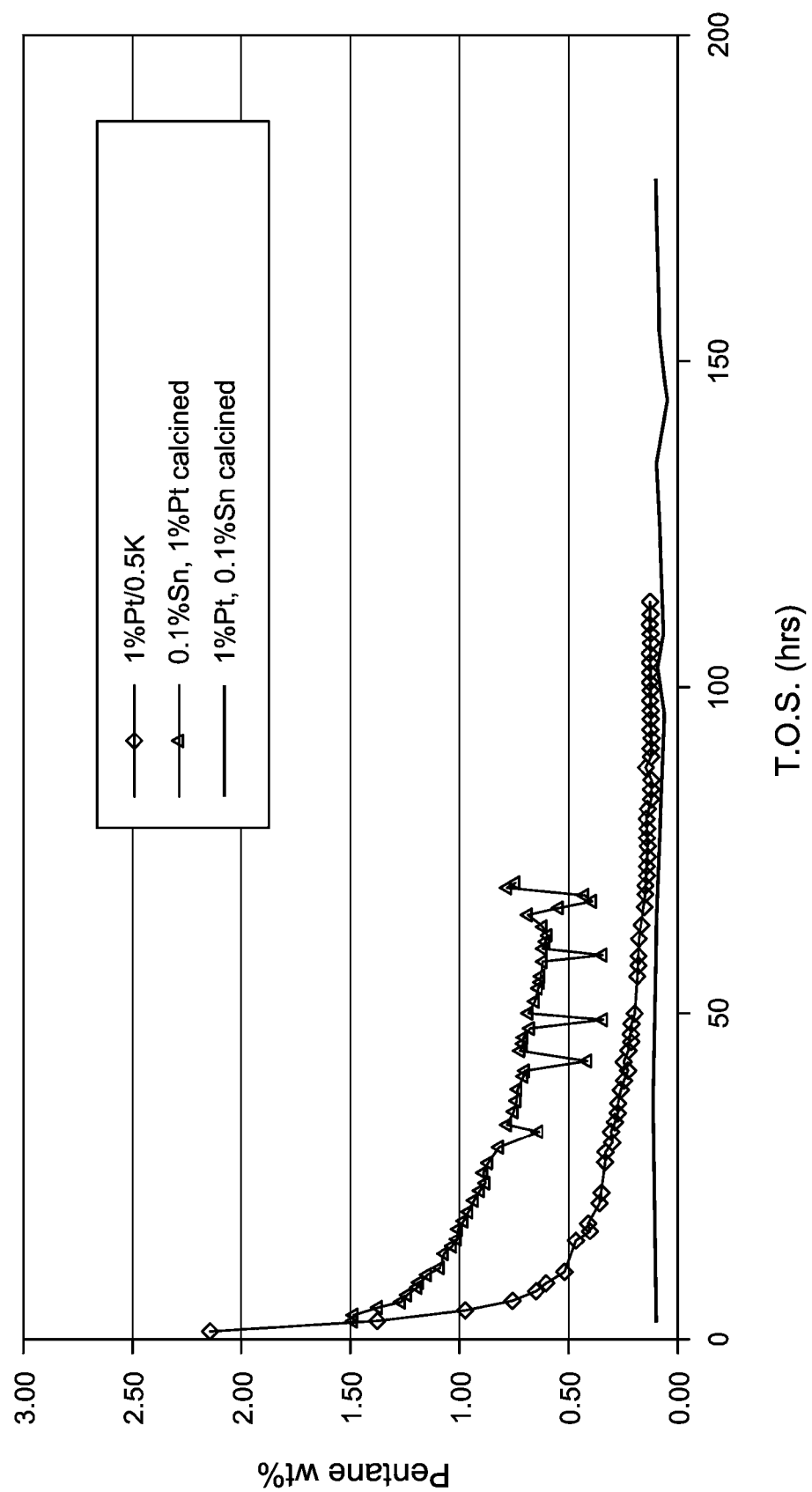
FIG. 7 is a graph comparing pentane production against time on stream for the calcined 1% Pt/0.1% Sn/SiO$_2$ catalyst of Example 4 with that of the calcined 0.1% Sn/1% Pt/SiO$_2$ catalyst of Example 2B and that of the calcined 1% Pt/0.5% K/SiO$_2$ catalyst of Comparative Example 1.
Figure 8:
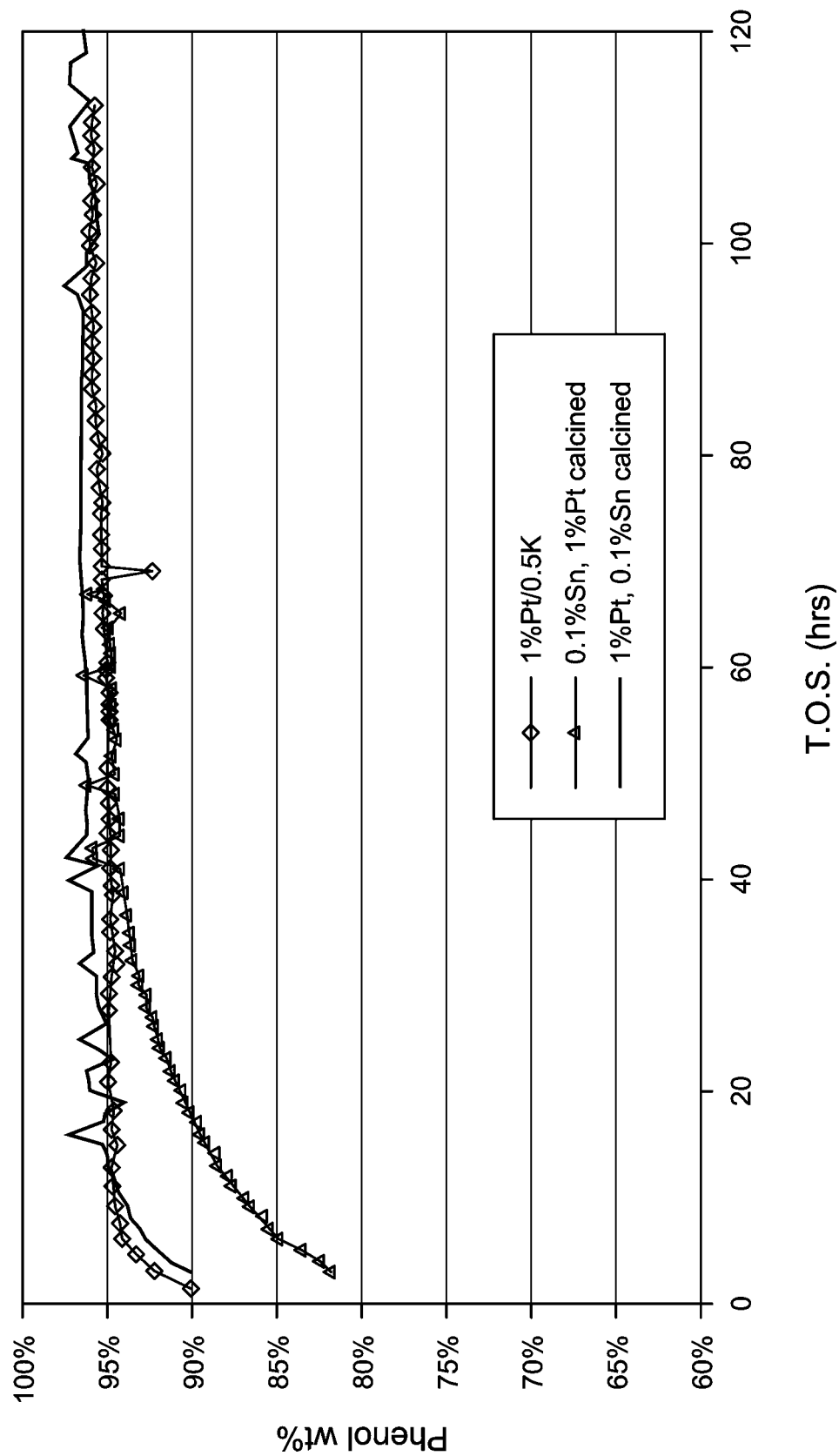
FIG. 8 is a graph comparing phenol production against time on stream for the calcined 1% Pt/0.1% Sn/SiO$_2$ catalyst of Example 4 with that of the calcined 0.1% Sn/1% Pt/SiO$_2$ catalyst of Example 2B and that of the calcined 1% Pt/0.5% K/SiO$_2$ catalyst of Comparative Example 1.

The data show that the addition sequence of the Pt and Sn did not affect the catalyst activity and stability, both catalysts showing similar cyclohexanone conversion and similar catalyst deactivation. Thus, the calcined 0.1% Sn/1% Pt/SiO$_2$ catalyst of Example 2B and the calcined 1% Pt/0.1% Sn/SiO$_2$ catalyst of Example 8 show similar improvement in the catalyst activity and stability as compared with the Pt/K catalyst of Comparative Example 1 (FIG. 6). Unexpectedly, however, the Sn addition sequence dramatically affects the pentane formation. Thus, as shown in FIG. 7, when the Sn was added first then the Pt as in Example 8, the catalyst showed reduced pentane production and pentylbenzene was below GC detection limit as compared to the catalyst of Example 2B, where Pt was added to the support first then the Sn. Similarly, FIG. 8 shows that better selectivity to phenol was observed with the catalyst of Example 8 (Sn added first) as compared to the catalyst of Example 2B (Pt added first).

Figure 9:
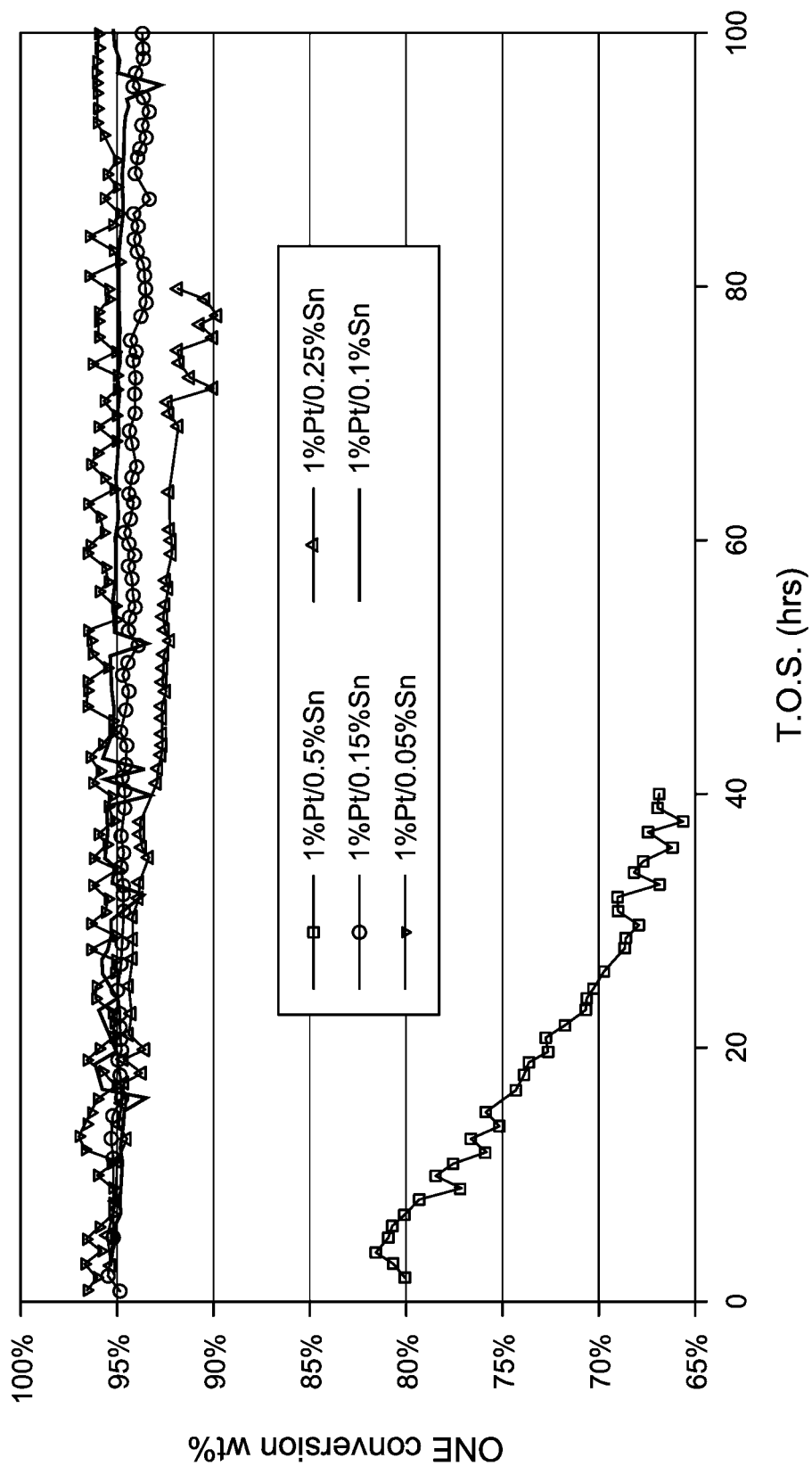
FIG. 9 is a graph comparing cyclohexanone conversion against time on stream for the calcined 1% Pt/x % Sn/SiO$_2$ catalysts of Examples 3 to 8.

FIG. 9 demonstrates the addition of Sn in amounts in excess of 0.15 wt % has a deleterious effect on catalyst stability and activity. Both 0.05 wt % and 0.1 wt % Sn catalyst showed similar catalyst deactivation.

Figure 10:
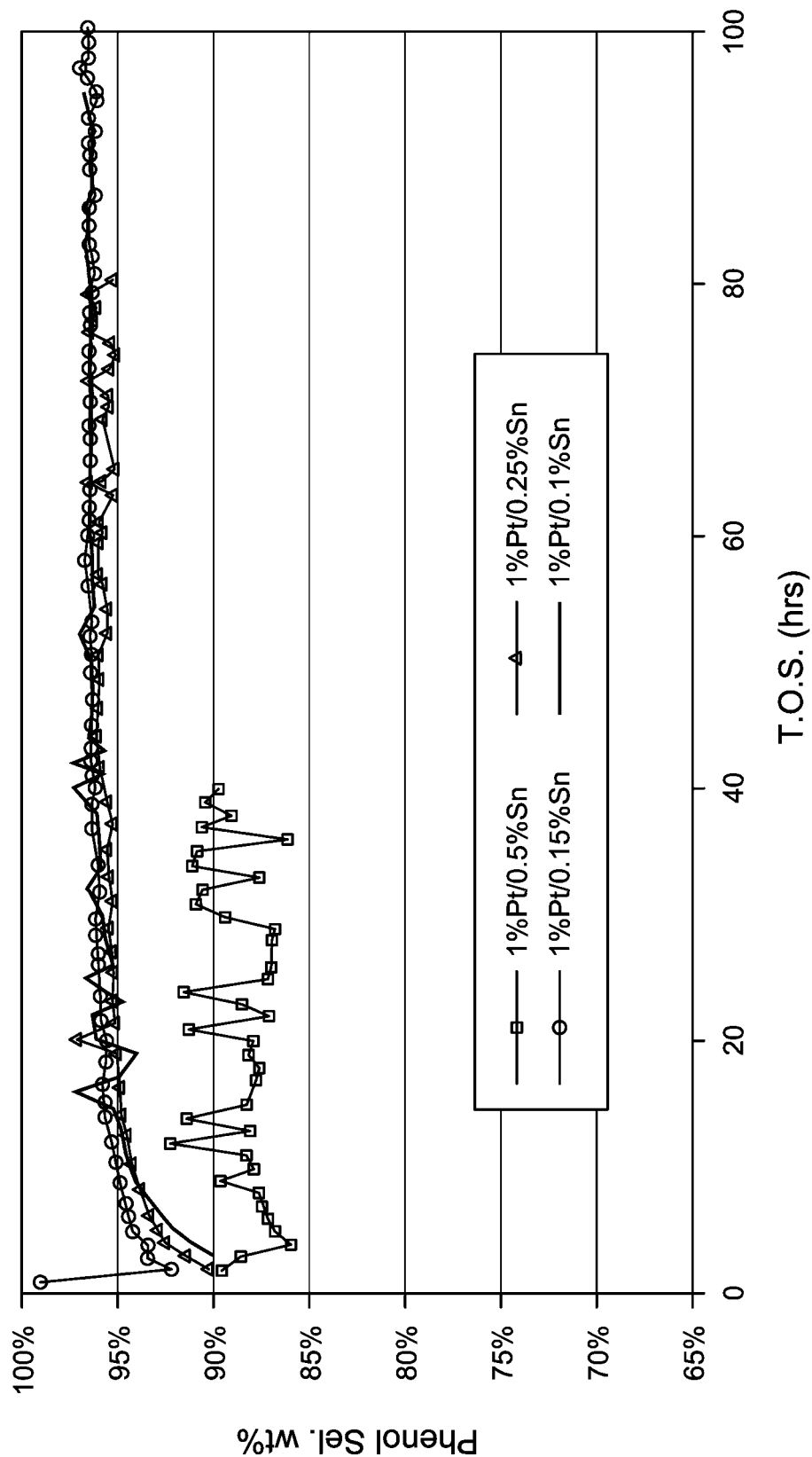
FIG. 10 is a graph comparing phenol production against time on stream for the calcined 1% Pt/x % Sn/SiO$_2$ catalysts of Examples 3 to 8.

FIG. 10 demonstrates that catalysts which contain <0.25 wt % Sn show similar phenol selectivity, whereas FIG. 11 demonstrates that increasing the Sn content lowers the selectivity of the catalyst to pentane formation. The pentylbenzene selectivity was consistently below the GC detection limit.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A composition comprising:
   (a) at least 99 wt % phenol; and
   (b) 0.1 wppm to 10 wppm of pentenylbenzene, wherein the wt % and wppm are based upon the total weight of the composition.

2. The composition of claim 1, wherein the composition further comprises 0.1 wppm to 1000 wppm of at least one of the following components: n-butylbenzene, n-pentylbenzene, hexanone, cyclohexenol, and methylcyclopentenone, based upon the total weight of the composition.

3. The composition of claim 1, wherein the composition further comprises 0.1 wppm to 1000 wppm of at least one of the following components: bicyclohexane, cyclohexylbenzene, methylcyclopentylbenzene, hydroxycyclohexanone, cyclohexanone, cyclohexanol, cyclohexanone, cyclohexanedione, benzoic acid, hexanal, and methylcyclopentanone, based upon the total weight of the composition.

4. The composition of claim 2, wherein the composition comprises 0.1 wppm to 10 wppm of each one of pentylbenzene, n-butylbenzene, n-pentylbenzene, hexanone, cyclohexenol, and methylcyclopentenone, based upon the total weight of the composition.

5. The composition of claim 1, wherein the composition comprises 0.1 to 3 wppm of pentenylbenzene, and further comprises 0.1 to 3 wppm of at least one of: hydroxycyclohexanone, cyclohexenone, cyclohexanol, cyclohexanone, cycloheanedione, benzoic acid, hexanol, methylcyclopentanone, hexanone, hexanone, cyclohexenol, and methylcyclopentenone, based upon total weight of the composition.

6. The composition of claim 1, wherein the composition comprises at least 99.90 wt % phenol, based upon the total weight of the composition.

7. The composition of claim 1, wherein the composition further comprises 0.1 wppm to 1000 wppm water as measured according to ASTM D 1631, based upon the total weight of the composition.

8. The composition of claim 1, wherein the composition comprises less than 1 wppm of each of hydroxyacetone, mesityl oxide, 2-methylbenzofuran, acetophenone, alpha-methylstyrene, cumene, 2-phenylpropanal, tert-butylbenzene, and sec-butylbenzene.

9. The composition of claim 1, wherein the composition contains no measurable concentration of any of hydroxyacetone, mesityl oxide, 2-methylbenzofuran, acetophenone, alpha-methylstyrene, cumene, 2-phenylpropanal, tert-butylbenzene, or sec-butylbenzene.

10. The composition of claim 1 having at least one of:
    (a) a density of 1.047 to 1.053 g/ml as determined according to ASTM D 3505;
    (b) a freezing point of at least 40.6° C. as determined according to ASTM D1493;
    (c) a color in the molten state of not greater than 20 as determined by ASTM D1686-10;
    (d) a Sulfuric Acid Discoloration of at least 95%; and
    (e) a cresol content of less than 10 wppm based upon total weight of the composition.

11. A composition comprising:
    (a) at least 99.99 wt % phenol;
    (b) at least 0.1 wppm to 10 wppm of at least one of bicyclohexane, cyclohexylbenzene, methylcyclopentylbenzene, n-butylbenzene, n-pentylbenzene, and pentenylbenzene; and
    (c) at least 0.1 wppm to 3 wppm of at least one of: hydroxycyclohexanone, cyclohexenone, cyclohexanol, cyclohexanone, cyclohexanedione, benzoic acid, hexanal, and methylcyclopentanone, wherein the wt % and wppm are measured according to ASTM D6142 and are based upon the total weight of the composition, and wherein the total amount of the hydrocarbon components and oxygenate components present in the composition accounts for at least 10 wt % of the total amount of contaminants present in the composition.

* * * * *